US012577319B2

(12) United States Patent
Zhu et al.

(10) Patent No.: US 12,577,319 B2
(45) Date of Patent: Mar. 17, 2026

(54) ANTI-TROP2 ANTIBODY

(71) Applicants: SICHUAN BAILI PHARM CO. LTD, Sichuan (CN); CHENGDU DUOTE ANTIBODY PHARMACEUTICAL CO., LTD., Sichuan (CN)

(72) Inventors: Yi Zhu, ChengDu (CN); Yong Zhang, ChengDu (CN); Shi Zhuo, ChengDu (CN); Muran Ding, ChengDu (CN); Zun Wang, ChengDu (CN)

(73) Assignee: SYSTIMMUNE, INC., Redmond, WA (US)

( * ) Notice: Subject to any disclaimer, the term of this patent is extended or adjusted under 35 U.S.C. 154(b) by 613 days.

(21) Appl. No.: 18/011,175

(22) PCT Filed: Jun. 18, 2021

(86) PCT No.: PCT/CN2021/100903
§ 371 (c)(1),
(2) Date: Dec. 19, 2022

(87) PCT Pub. No.: WO2021/259162
PCT Pub. Date: Dec. 30, 2021

(65) Prior Publication Data
US 2023/0242665 A1 Aug. 3, 2023

(30) Foreign Application Priority Data
Jun. 22, 2020 (CN) .......................... 202010573040.0

(51) Int. Cl.
*C07K 16/30* (2006.01)

(52) U.S. Cl.
CPC .......... *C07K 16/30* (2013.01); *C07K 2317/24* (2013.01); *C07K 2317/565* (2013.01); *C07K 2317/92* (2013.01)

(58) Field of Classification Search
CPC ...................................................... C07K 16/30
See application file for complete search history.

(56) References Cited

FOREIGN PATENT DOCUMENTS

| CN | 107428837 A | 12/2017 |
| CN | 107446050 A | 12/2017 |
| WO | WO 2013082254 A | 6/2013 |
| WO | WO 2014193999 A | 12/2014 |

OTHER PUBLICATIONS

Thornburg et al., Journal of Clinical Investigation. vol. 123 (10): 4405-4409; 2013 (Year: 2013).*
GenBank: AGC24859.1; 2013 (Year: 2013).*
(Continued)

*Primary Examiner* — Sue X Liu
(74) *Attorney, Agent, or Firm* — EpiMED LLC

(57) ABSTRACT

The present disclosure relates to antibodies, in particular monoclonal antibodies of murine, chimeric, and humanized origin, that specifically bind to the human TROP2 protein, and to the amino acid and nucleotide sequences encoding these antibodies. The disclosure also discloses the use of these antibodies as a diagnostic reagent or a drug in the diagnostic and/or therapeutic management of malignancies or any lesion related to the overexpression of the receptor.

19 Claims, 15 Drawing Sheets
Specification includes a Sequence Listing.

(56) References Cited

OTHER PUBLICATIONS

Asakura. K. et al. "immunoglobulin heavy chain. partial [Mus musculus domesticus]" GenBank: AAB38065.I, Dec. 5, 1996 (Dec. 5, 1996), pp. 1-2.

Campbell, M.J. et al. "immunoglobulin kappa chain, partial [Mus musculus]" GenBank: AAA38841.2, Jul. 26, 2016 (Jul. 26, 2016) pp. 1.

Hu, D.C. et al. "anti-CD4 immunoglobulin heavy chain variable region, partial [Mus musculus]" GenBank: AFB71081.I, Oct. 6, 2012 (Oct. 6, 2012), pp. 1-2.

Fan, Q. et al. "immunoglobulin kappa light chain [synthetic construct]" GenBank: BCA37475.I, Feb. 13, 2020 (Feb. 13, 2020), pp. 1.

Kunihiko. A. et al. "Oligodendrocyte-reactive 01. 04. and HNK-1 monoclonal antibodies are encoded by germline Immunoglobulin genes" Molecular Brain Research, vol. 34, Dec. 31, 1995 (Dec. 31, 1995), pp. 283-293.

"Preparation of A Full Human Anti-Trop-2 IgG and Its Effect on Ovarian Cancer Cells" Acta Universitatis Medicinalis Nanjing (Natural Science). vol. 36, No. 3, Mar. 31, 2016 (Mar. 31, 2016), pp. 280-286.

* cited by examiner

7F11-chimeric                    4D3-chimeric

7F11-chimeric                    4D3-chimeric

| | 4D3-humanized | | | |
|---|---|---|---|---|
| | Day 0 | Day 7 | Day 14 | Day 21 |
| Aggregate | 0.46% | 0.51% | 0.53% | 0.62% |
| Monomer | 99.54% | 99.49% | 99.47% | 99.38% |

ANTI-TROP2 ANTIBODY

CROSS-REFERENCE TO RELATED APPLICATION

This application is a national stage application of international application number PCT/CN2021/100903, filed Jun. 18, 2021, titled "Anti-trop2 Antibody", which claims the priority benefit of Chinese Patent Application No. 202010573040.0, filed on Jun. 22, 2020, which is hereby incorporated by reference in its entirety.

TECHNICAL FIELD

The present disclosure relates to antibodies that can specifically bind to human TROP2 protein, especially monoclonal antibodies of murine, chimeric and humanized origin, and the amino acid and nucleotide sequences encoding these antibodies. The present disclosure also encompasses the use of these antibodies as diagnostic reagents or drugs in the diagnostic and/or therapeutic treatment of malignant tumors or any pathological changes related to the overexpression of the receptor.

BACKGROUND

The Trop2 protein, also known as trophoblast antigen 2 or tumor associated calcium signal transducer 2, is encoded by a single-copy gene TACSTD2 on chromosome 1p32. The corresponding mRNA synthesizes a 36 kDa nascent polypeptide, which, after N-terminal glycosylation, forms a monomeric membrane protein with a single transmembrane domain (Annie R. A. et al., 2015).

Within 26 amino acid length, intracellular region of TROP2, there is a serine site at position 303, which is highly conserved among species (Basu et al., 1995; Annie R A et al., 2015) and can be phosphorylated by PKC kinase, and becomes the binding site for the signal transduction molecule $PIP_2$ downstream that stimulates the increase of cytoplasmic calcium concentration (Sewedy et al., 1998; Alberti. et al., 1999). When overexpressed in in vitro cell lines, the Trop2 protein lacking the cytoplasmic region is deprived its growth-stimulating function, indicating a stimulatory effect of the Trop2 cytoplasmic region on other signaling pathways (Guerra. et al. 2013). The extracellular region of Trop2 contains a structural domain capable of binding EGF growth factor, which may potentially intercept EGF to downregulate the activity of the IGF-1R/Akt signaling pathway. Therefore, a decrease in Trop2 expression may reversely activate the IGF-1R/Akt signaling pathway (Lin. et al., 2011; Annie R A et al., 2015).

Trop2 plays a significant role in promoting tumorigenesis. Overexpression of Trop2 can significantly enhance the tumorigenicity of NIH3T3 cells (Wang. et al., 2008). Trop2 can also affect epithelial-mesenchymal transition (EMT) and enhance the migration and invasion capabilities of cancer cells (Trerotola. et al., 2013; Li. et al., 2017). This process may be achieved by affecting the PI3K/Akt signaling pathway: in the gallbladder cancer cells that overexpress Trop2, the activation of Akt phosphorylation is significantly increased; conversely, knocking down the expression of Trop2 can inhibit the activity of this signaling pathway (Li. et al., 2017). In addition, the overexpression of Trop2 can also stimulate the activity of MAPK/ERK signaling pathway, which up-regulates the proliferation of pancreatic cancer cells and increase tumor progression in tumor-bearing mice (Cubas. et al., 2010).

The expression of Trop2 protein is found in a series of epidermal-derived tissues, such as breast, kidney, and pancreas during embryonic development and adulthood (Annie R. A. et al., 2015). However, in the tumors of those corresponding normal tissues, the expression of the Trop2 protein is significantly increased and is in a positive correlation with the progression of tumor growth in animal models (Trerotola. et al., 2013). Since the Trop2 gene sequence itself is not mutated or amplified, the upregulation of the Trop2 expression in cancer is considered to be caused by stimulation at the level of transcriptional regulation (Trerotola. et al., 2013). In patients with different types of parenchymal tumors, the overexpression of this protein usually predicts the poor prognosis of the tumor (Zeng. et al., 2016). In gallbladder cancer (Chen. et al., 2014), gastrointestinal cancer (Muhlmann. et al., 2009), hilar cholangiocarcinoma (Ning. et al., 2013) and pancreatic cancer (Fong. et al., 2008)), the survival rate of patients with Trop2 high expression disease is significantly reduced. In view of the high-level expression of Trop2 in a variety of cancers and its significant impact on the survival rate of patients, this protein is considered to be a potential target for cancer therapy.

Among known antibody drugs, there is a toxin-coupled antibody (antibody-conjugated drugs, ADC) against the Trop2 target: IMMU-132 (Goldenberg. et al., 2015). The antibody RS7 of this ADC was obtained by means of hybridoma preparation and fusion screening of mouse spleen lymphocytes immunized with crude lung cancer cell membrane extracts and mouse myeloma cells (Stein. et al., 1990). In the crude extract, the antigen bound by RS7 was later proved to be Trop2 (Stein. et al., 1994). The RS7 antibody itself can be endocytosed by a variety of cancer cells, thus RS7 antibody has the potential to be prepared as ADC (Stein. et al., 1993). After the sequential humanization of murine-derived RS7, humanized versions of RS7 were used to prepare antibody-conjugated drugs and loaded with the SN-38 drug, a topoisomerase inhibitor (Moon, et al., 2008; Sahota. et al., 2017), by means of interchain sulfhydryl coupling. In the recent clinical phase I data, IMMU-132 was shown to be clinical effective in the treatment of multiple cancers, especially triple-negative breast cancer (Starodub. et al., 2015; Sahota and Vahdat., 2017).

The information disclosed in this application relates to the field of therapeutics. Specifically, the chimeric antibody or humanized antibody described in this application can bind to human type II trophoblast antigen protein (Trop2) and functions as a targeting antibody in antibody-coupled drug therapy.

SUMMARY

The present disclosure does not involve natural forms of antibodies. The antibodies involved in the present disclosure are all obtained through immunization of mice, identification, and isolation, or through genetic recombination methods. According to the present disclosure, the object of protection is an antibody or a functional fragment or derivative, and the antibody is characterized by comprising at least one complementarity-determining region (CDR) whose amino acid sequence corresponds to any of SEQ ID No: 1 to SEQ ID No: 12.

If any antibody fragment or derivative contains at least one CDR, and the CDR has at least 80% identity, or preferably 85%, 90%, 95%, or 98% identity, after optimized comparison with the sequence SEQ ID No: 1 to SEQ ID No:

12, the antibody fragment or derivative should be understood as equivalents of the application, and therefore also a part of the application.

In one embodiment, the antibody or its functional fragments or derivatives disclosed herein comprises a heavy chain, and the heavy chain comprises at least one CDR, and the CDR contains the amino acid sequence from SEQ ID No: 1 to SEQ ID No: 6.

In a further embodiment, the antibody or its functional fragments or derivatives disclosed herein comprises a light chain, and the light chain comprises at least one CDR, and the CDR contains the amino acid sequence from SEQ ID: 7 to SEQ ID No: 12.

Accordingly, in one embodiment, the antibody or its functional fragments or derivatives disclosed herein comprises a heavy chain comprising CDR-H1, CDR-H2, and CDR-H3, wherein the CDR-H1 includes the amino acid sequence from SEQ ID No: 1, the CDR-H2 includes the amino acid sequence from SEQ ID No: 2, and the CDR-H3 includes the amino acid sequence from SEQ ID No: 3.

More specifically, in one embodiment, the antibody or one of its functional fragments or derivatives comprises a heavy chain and, in the heavy chain, a chimeric antibody comprises SEQ ID No: 13, a humanized antibody contains SEQ ID No: 17.

Accordingly, in a further embodiment, the antibody or one of its functional fragments or derivatives disclosed herein comprises a light chain comprising CDR-L1, CDR-L2, and CDR-L3, wherein the CDR-L1 includes the amino acid sequence from SEQ ID No: 7, the CDR-L2 includes the amino acid sequence from SEQ ID No: 8, and the CDR-L3 includes the amino acid sequence from SEQ ID No: 9.

More specifically, in one embodiment, the antibody or one of its functional fragments or derivatives comprises a light chain and, in the light chain, a chimeric antibody comprises SEQ ID No: 14, a humanized antibody contains SEQ ID No: 18.

Accordingly, in a further embodiment, the antibody or one of its functional fragments or derivatives disclosed herein comprises a heavy chain comprising CDR-H1, CDR-H2, and CDR-H3, wherein the CDR-H1 includes the amino acid sequence from SEQ ID No: 4, the CDR-H2 includes the amino acid sequence from SEQ ID No: 5, and the CDR-H3 includes the amino acid sequence from SEQ ID No: 6.

More specifically, in a further embodiment, the antibody or one of its functional fragments or derivatives comprises a heavy chain and, in the heavy chain, a chimeric antibody comprises SEQ ID No: 15, a humanized antibody contains SEQ ID No: 19.

Accordingly, in a further embodiment, the antibody or one of its functional fragments or derivatives disclosed herein comprises a light chain comprising CDR-L1, CDR-L2, and CDR-L3, wherein the CDR-L1 includes the amino acid sequence from SEQ ID No: 10, the CDR-L2 includes the amino acid sequence from SEQ ID No: 11, and the CDR-L3 includes the amino acid sequence from SEQ ID No: 12.

More specifically, in a further embodiment, the antibody or one of its functional fragments or derivatives comprises a light chain and, in the light chain, a chimeric antibody comprises SEQ ID No: 16, and a humanized antibody contains SEQ ID No: 20.

As another aspect of the application, the application provides isolated DNA, which features a nucleic acid selected from the following DNA sequences: the nucleic acid encoding any amino acid sequences of SEQ ID No: 1 to SEQ ID No: 20.

More specifically, the application provides a nucleic acid selected from the following DNA sequences:

One embodiment includes the nucleic acid sequences of SEQ ID No: 21, SEQ ID No: 22, SEQ ID No: 23, or SEQ ID No: 27, SEQ ID No: 28, SEQ ID No: 29.

A further embodiment includes the nucleic acid sequences of SEQ ID No: 24, SEQ ID No: 25, SEQ ID No: 26, or SEQ ID No: 30, SEQ ID No: 31, and SEQ ID No: 32.

More specifically, in one embodiment, a chimeric antibody includes the amino acid sequence encoded by the nucleic acid sequence of SEQ ID No: 33 and SEQ ID No: 34, and a humanized antibody includes the amino acid sequence encoded by the nucleic acid sequences of SEQ ID No: 37 and SEQ ID No: 38. In a further embodiment, the chimeric antibody includes the amino acid sequence encoded by the nucleic acid sequence SEQ ID No: 35 and SEQ ID No: 36, and the humanized antibody includes the amino acid sequence encoded by the nucleic acid sequence SEQ ID No: 39 and SEQ ID No: 40.

DETAILED DESCRIPTION

Figure 1:
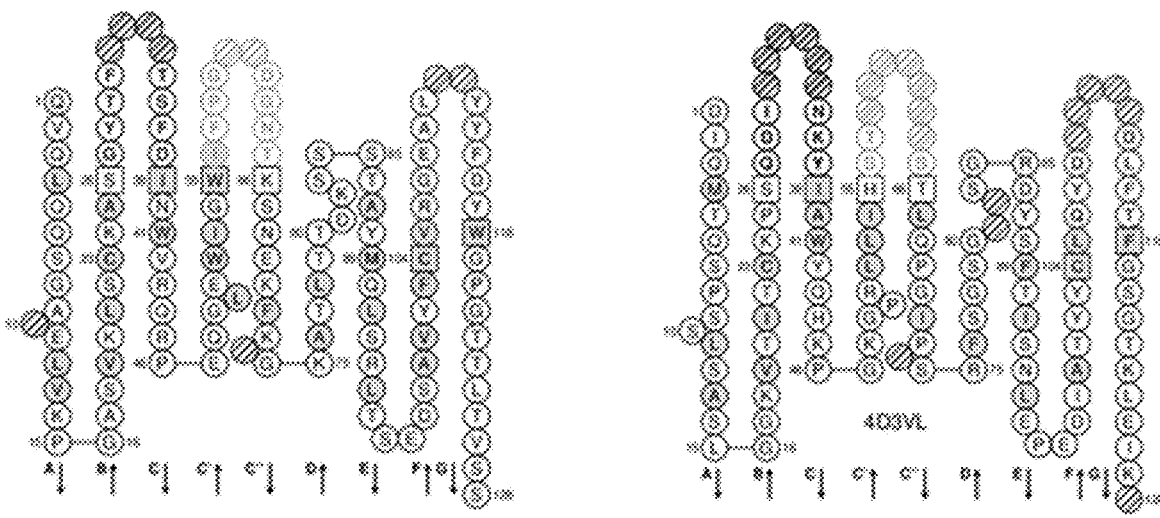
FIG. 1 shows the CDR region recognition and two-dimensional structure diagram of 4D3 light chain (SEQ ID NO: 14) and heavy chain (SEQ ID NO: 13) variable region.

Example 1 Immunization of Balb/c Mice with 6-8 Weeks of Age with TROP2 Antigen Construct an expression vector for the extracellular region of TROP2, and use suspension cell 293F to transiently express milligram-level TROP2 protein. Select 6-8 weeks old mice, perform subcutaneous immunization with TROP2 antigen according to the immunization dose and time points shown in the following table, and select the mice with the highest plasma titer after three immunizations. The immunization process is shown in Table 1.

| Procedure | Immunization progress (days) | Route and Dosage |
| --- | --- | --- |
| First Immunization | 0 | 100 ug/0.25 ml/each mouse, complete adjuvant, subcutaneous immunization |
| Second Immunization | 14 | 100 ug/0.25 ml/each mouse, incomplete adjuvant, subcutaneous immunization |
| Third Immunization | 35 | 100 ug/0.25 ml/each mouse, incomplete adjuvant, subcutaneous immunization |
| Blood Collection | 42 | Detection of tail vein plasma titer by ELISA with TROP2 antigen-coated plate |
| Final immunization | 56 | 50 ug/0.25 ml/each mouse, phosphate buffer saline, intraperitoneal immunization |

Example 2 In Vitro Fusion of Spleen Cells of Immunized Mice

Pre-culture mouse myeloma cells SP2/0 in DMEM+FBS 10% complete medium. Before fusion, use a Pasteur pipette to blow out $5 \times 10^7$ SP2/0 cells, centrifuge at 1000 g, 5 min, and hot rinse residual serum with 37° C. preheated serum-free DMEM, while collecting the KM mouse feeder cells in the abdominal cavity, and plate the feeder cells in 96 well plates at $5 \times 10^3$ cells/100 ul/well. On the 3rd day after the final immunization, blood was collected from the eyeballs, and the final immunized mice were sacrificed. After being soaked in 75% alcohol, the mice were placed on a sterile operating table to retrieve the spleen tissue. Use pre-warmed serum-free DMEM to blow out the spleen cells, take ½ of the spleen cells for counting, mix the spleen cells: SP2/0 cells at a ratio of 1:1 to 10:1, and suck up the remaining DMEM after centrifugation. Add 1 ml volume of preheated PEG-1450 and mix evenly, add 35 ml of preheated DMEM medium after 3 minutes to terminate the dilution. The cells were centrifuged at 1000 rpm for 5 min, and then resuspended in HAT screening medium, and plated in 10 96-well plates.

Example 3 Positive Detection of Hybridoma Cell Supernatant 7 to 10 days after fusion, observe the status of the cells forming clones. The medium was changed with DMEM+ 10% FBS medium one day before the supernatant test. At the same time, the ELISA plate was coated with TROP2 antigen at a concentration of 2ug/ml. On the day of the test, use a multi-channel electric pipette on a sterile operating table to suck the medium supernatant from the 96-well plate, and add it to the corresponding ELISA plate well. Incubate the ELISA plate at 37° C. for 1 hr, then wash the well plate 3 times with PBST, and add HRP-labeled goat anti-mouse antibody diluted 1:5000. After incubating at 37° C. for 1 hr, wash with PBST 3 times. Configure TMB substrate color developing solution, add 50 ul to each hole, and react at room temperature for 5-10 min. Then add 50 ul/well of 2M sulfuric acid solution to stop the color development. Screen positive clones according to the OD450 reading on the microtiter plate.

Example 4 Subclonal Screening of Positive Cell Lines

Label the wells of the fusion cell plate with a higher OD450 value and continue to culture for no more than 2 days. The feeder cells were plated according to the method in Embodiment 2, and the positive cells were blown evenly with a 200 ul pipette tip. Take no more than 5 ul cell suspension volume for subcloning, dilute it to 100 ul, and add to first well of the 96 well plate that contains 100 ul/well feeder cell suspension in advance. From the direction of A1 to H1, pipette evenly of a volume of 100 ul to the last row, and then use a multi-channel electric pipette to pipette 100 ul evenly from the direction of A1 to A12 to the last row. The well plates are cultured for 7-10 days, the wells formed by single clones are marked, and the supernatant positive detection is performed with reference to the method in the Embodiment 3.

Example 5 Preparation of Monoclonal Antibodies from Ascites 7 days before the preparation of ascites, the Balb/c mice were injected intraperitoneally with paraffin oil of 1 ml per mouse. Subsequently, the monoclonal cells with a stable positive rate after the first subcloning were picked and expanded for culture. Collect the cells when they grow to at least one well size of a 6-well plate, and rinse the cells 3 times with phosphate buffer at 1000 g for 3 min centrifugation. Preparation was made by injecting $1 \sim 2 \times 10^6$ per mouse per mouse. Feed the mice for 7-10 days and observe the abdominal cavity of the mice. Ascites was collected with an 18-gauge sterile needle, and the ascites fluid was collected at 14000 g at a rotation speed of 5 min. The obtained supernatant was purified by proteinA/G affinity column to obtain monoclonal antibodies for 4D3 and 7F11 cell lines.

Example 6 Obtaining 4D3 Antibody Light and Heavy Chain Variable Region Coding Sequence Cultivate the monoclonal cell line to a 6-well plate, and collect the cells with trizol when the confluence rate reaches 90-100%. Total RNA was extracted in an RNase-free environment, and oligo dT was used as a reverse transcription primer to synthesize a cDNA library. This cDNA library is used as a PCR template after the 5'end of the terminal transferase TdT plus dGTP. The upstream primer is oligo dC, and the downstream primer corresponds to the primer matching of the 5'-end CH1 constant region of the antibody light and heavy chain, with the help of high-fidelity enzyme primerSTAR Perform 5'-RACE amplification of variable region genes. The PCR products were analyzed by DNA agarose gel electrophoresis, and DNA fragments with a length of ~750 bp were recovered for downstream TA cloning. Strains that were identified as positive by colony PCR were sequenced. The obtained sequence was identified by the online IMGT database for sequence alignment and two-dimensional mapping of the variable region sequence.

Figure 2:
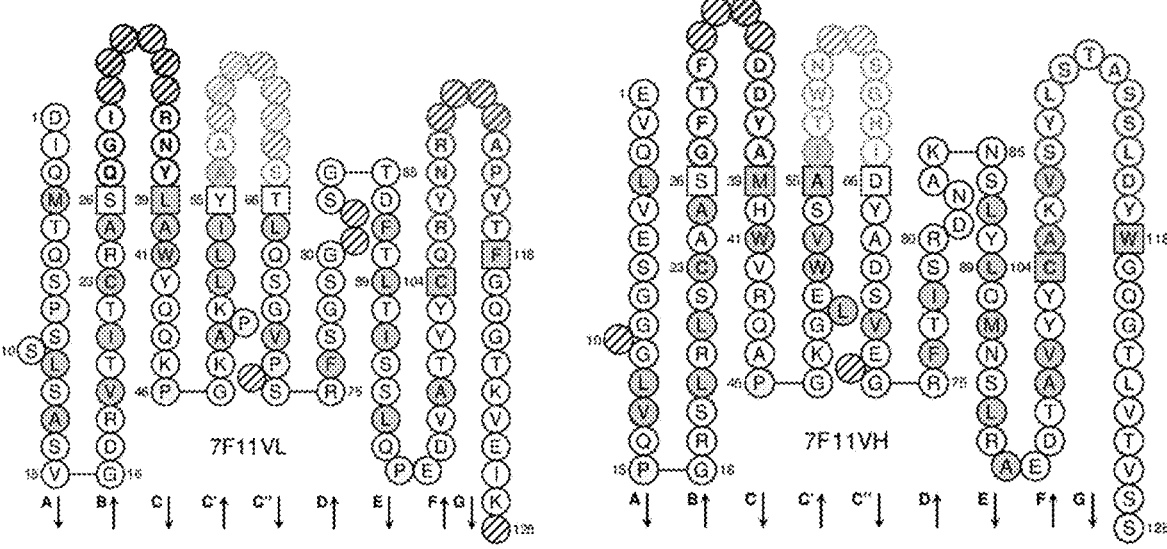
FIG. 2 shows the CDR region recognition and two-dimensional structure diagram of 7F11 light chain (SEQ ID NO: 16) and heavy chain (SEQ ID NO: 15) variable region.

Example 7 Obtaining 7F11 Antibody Light and Heavy Chain Variable Region Coding Sequence Refer to the operation process in Embodiment 6 to obtain the light and heavy chain variable region sequence of the 7F11 clone, as shown in FIG. 2.

Example 8 Expression and Purification of Antibody

Freestyle™ 293-F (Invitrogen) suspension cells were used to express the antibodies. One day before transfection, inoculate cells at a density of $6\times10^5$ cells/mL in a 1 L shake flask containing 300 mL F17 complete medium (Freestyle™ F17 expression medium, Gibco), 37° C., 5% $CO_2$, 120 rpm cell culture shake Incubate in a bed overnight. The next day, the antibody expression plasmid was transfected with PEI, where the ratio of plasmid:PEI was 2:1. One day after transfection, TN1 feed medium was added at 2.5% (v/v), the culture was continued for 4 days, and the supernatant was collected by centrifugation. The obtained expression supernatant was collected and passed through a Protein A affinity chromatography column (Mabselect Sure LX, GE), eluted with 0.1M citric acid (pH3.0), and the captured antibody was washed with 1M Tris-HCl (pH9.0) Adjust to pH 7.0 by 1/10 (v/v), and pass the gel filtration chromatography column SEC (Superdex 200, GE) to remove impurities such as polymer and endotoxin, and at the same time replace the antibody buffer with PBS (pH7.4). The antibody obtained by this method has the target antibody monomer (POI %) greater than 99%, and is used for subsequent experiments.

Example 9 ELISA Method to Evaluate Antibody Affinity

The variable region gene was cloned into an expression plasmid containing the constant region of a human antibody, and the eukaryotic cell 293F was transiently transfected according to the protocol of Embodiment 8 and the secreted 4D3 and 7F11 chimeric antibodies were purified. Dilute the chimeric antibody to a concentration of 50ug/ml, add it to wells A1~H1 on the TROP2-coated ELISA plate, and then perform a 3-fold horizontal dilution from A1 to A12; incubate at 37° C. for 1 hr, then rinse and add Mouse anti-human Fc HRP-labeled antibody was incubated at 37° C. for color development.

Figure 3:
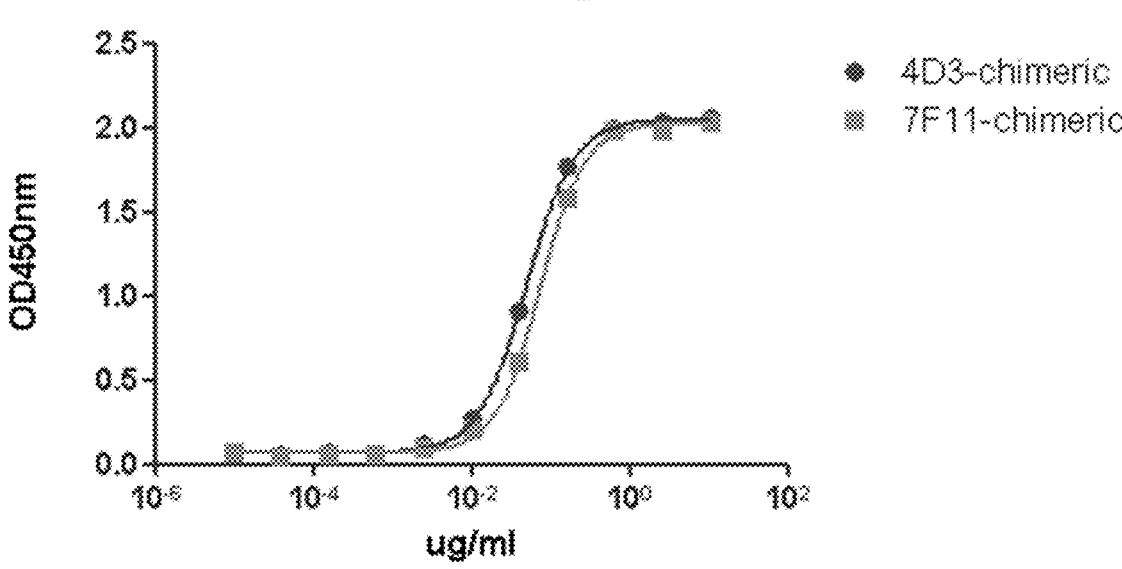
FIG. 3 shows the ELISA binding curve of ch4D3 and ch7F11.

FIG. 3 shows that 4D3 and 7F11 have good relative affinity. EC50(B4): 0.047 ug/ml; EC50(B7): 0.071 ug/ml.

Example 10 Evaluation of Antibody Biological Activity by Cell Immunofluorescence Method The BXPC-3 cells were plated and grown for 24 to 48 hours, so that the cell confluence rate in the 96-well cell culture plate reached 40 to 50%. On the day of the experiment, the supernatant was aspirated and washed twice. Add 3% BSA content PBS solution and block at 37° C. for 1 hr. Dilute the chimeric antibody and hRS7 antibody to 10ug/ml and incubate at 37° C. for 1 h, aspirate the primary antibody solution, wash 4 times, add 4% paraformaldehyde solution, 100 µL/well and stand at room temperature for 20 min, repeat washing twice, according to the ratio of 1:800, dilute the secondary antibody with 1% BSA solution, 100 ul/well.

Aspirate and discard the secondary antibody suspension, repeat washing 4 times, add 100 µL/well of DAPI dye solution at a concentration of 2 µg/ml, and incubate for 5 min at room temperature in the dark. Aspirate and discard the DAPI staining solution, and after repeated washing 4 times, add 1×DPBS solution, 100 µL/well, observe under a fluorescence microscope, and take pictures to record the experimental results.

Figure 4:
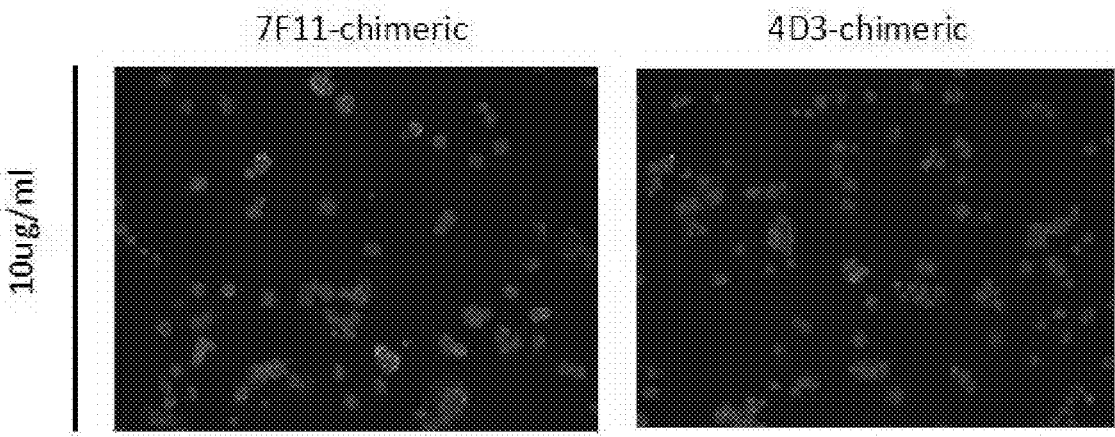
FIG. 4 shows a graph showing the cell surface binding activity of ch4D3 and ch7F11.

FIG. 4: Cell surface binding activity of ch4D3 and ch7F11 under the same antibody concentration and treatment conditions.

Example 11 Cell Endocytosis Method to Evaluate Antibody Biological Activity

Figure 5:
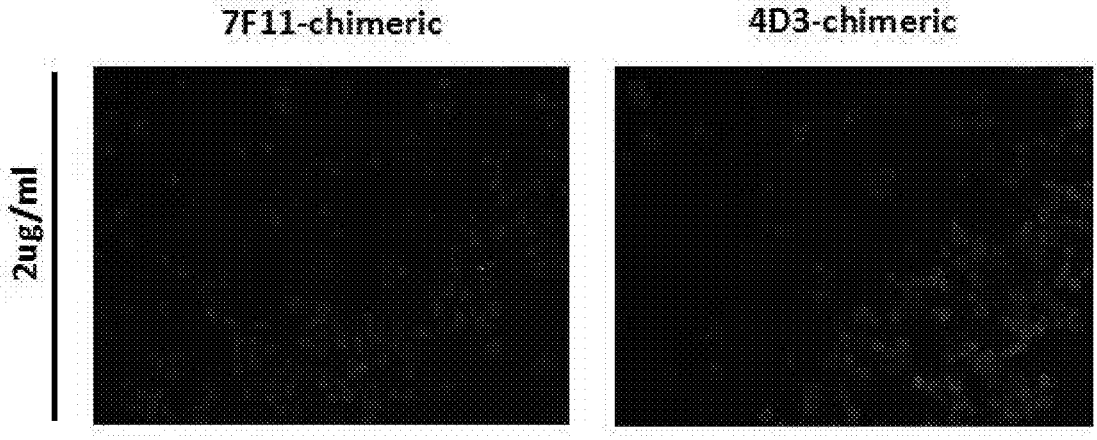
FIG. 5 shows a diagram showing the endocytosis activity of ch4D3 and ch7F11 antibodies on BXPC-3 living cells.

Follow the method in Embodiment 10 to plate BXPC-3 cells. On the day of the experiment, aspirate the cell culture solution, add PBS solution, and repeat the washing twice. Dilute the chimeric antibody and hRS7 antibody to 10ug/ml in a medium containing 1% FBS and incubate at 4° C. for 1 hour, aspirate the primary antibody solution, add complete medium for cell culture to be tested, and incubate at 37° C. for 1 hour. Aspirate and discard the cell culture medium, and after repeated washing 4 times, add 4% paraformaldehyde solution at 100 µL/well and let it stand for 20 min. After repeated washing twice, 3% BSA blocking solution containing 0.5% Triton-X100 was added, 100 µL/well, and allowed to stand at room temperature for 1 hour. Aspirate and discard the punching solution, and repeat the washing 2 times. Dilute the anti-human IgG fluorescent secondary antibody at a ratio of 1:800; 100 µL/well, incubate at 37° C. for 1 h. Aspirate and discard the fluorescent secondary antibody solution, repeat washing 4 times and then perform DAPI staining, and let it stand for 15 minutes at room temperature in the dark. Repeat washing 4 times, add 1×DPBS solution, 100 µL/well, observe the fluorescent staining results under a fluorescent microscope, as shown in FIGS. 4 and 5.

Example 12 Transformation of 4D3 Humanized Sequence

Obtain the nucleic acid sequence sequencing results of the 4D3 variable region, and enter the sequence into the V-QUEST sequence check window provided by the website IMGT (www.imgt.org). In order to obtain the sequence characteristics of the light and heavy chain variable regions, including three CDR region sequences and four FR region sequences, as well as the most closely related germline gene family sequences. In the IMGT-DomainGapAlign amino acid check window, search for the human germline gene family sequence with the highest sequence similarity. The 4D3 light chain corresponds to the human IGKV1-27*01+ IGKJ2*02 family sequence, and the 4D3 heavy chain corresponds to the human IGHV1-3* 01+IGHJ4*01 family sequence. Replace the CDR region on the human germline gene sequence with the CDR of the 4D3 light and heavy chain, and then use IMGT-Structural query to check the structure of the antibody. Finally, the 4D3-Hum version of the humanized sequence of light and heavy chains was obtained. Enter the 4D3 mouse sequence and humanized sequence into the online website to evaluate the similarity score of human antibodies.

Figure 6:
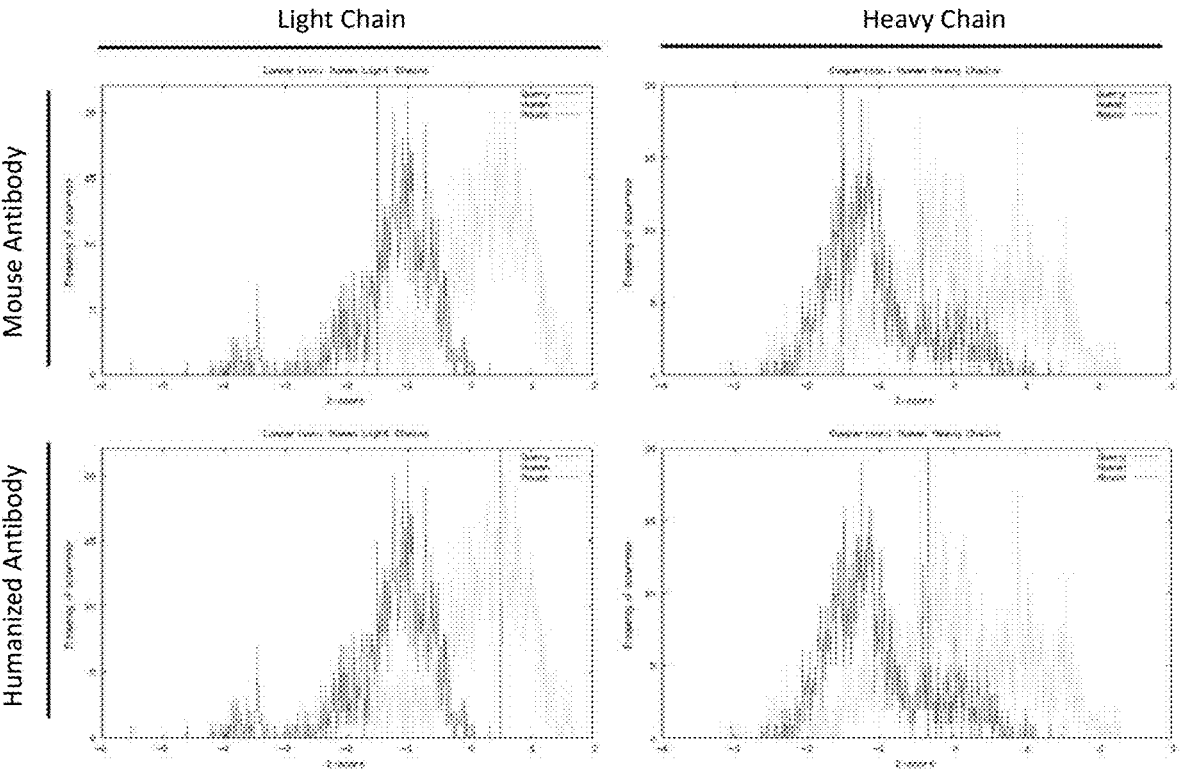
FIG. 6 shows the light and heavy chain variable region sequence of the 4D3 murine antibody, and its humanness (Z-score) changes before and after humanization.

In FIG. 6, the blue line represents the Z-score distribution range and frequency of the mouse antibody library, and the green line represents the Z-score distribution range and frequency of the human antibody library. The red straight line represents the Z-score obtained by the 4D3 light chain and heavy chain. After humanization, the Z-score of 4D3 increased significantly.

Example 13 7F11 Humanized Sequence Modification

Refer to the operation procedure in Embodiment 12 to obtain the humanized sequence of the light and heavy chains of the 7F11 mouse antibody. Enter the 7F11 mouse sequence and humanized sequence into the online website to evaluate the similarity score of human antibodies.

Figure 7:
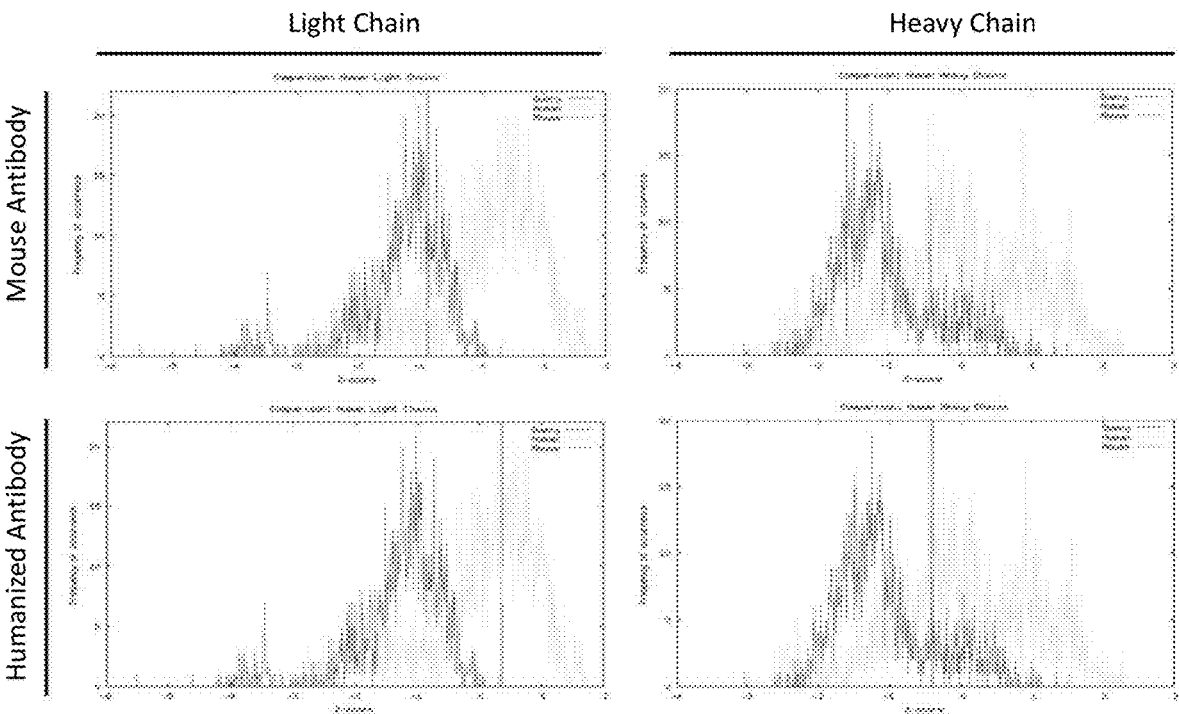
FIG. 7 shows the light and heavy chain variable region sequence of the 7F11 murine antibody, and its humanness (Z-score) changes before and after humanization.

The blue line in FIG. 7 represents the Z-score distribution range and frequency of the mouse antibody library, and the green line represents the Z-score distribution range and frequency of the human antibody library. The red straight line represents the Z-score obtained by the 4D3 light chain and heavy chain. After humanization, the Z-score of 7F11 has increased significantly.

Example 14 Relative Affinity Analysis of 4D3 Humanized Antibody

The 4D3 humanized antibody sequence was cloned into a eukaryotic expression vector, and the eukaryotic cell 293F was transiently transfected according to the protocol of Embodiment 8. The purified antibodies are uniformly diluted to 2ug/ml, and added to the wells A1~H1 of the TROP2-coated ELISA plate together with the mouse antibody, and then diluted 3 times from the direction of A1~A12; After incubating at 37° C. for 1 hr, rinse, then add anti-human Fc HRP-labeled antibody, and incubate at 37° C. for color development. Finally, the relative affinities between ch4D3 and hum4D3 antibodies were compared by EC50 and curve shape.

Figure 8:
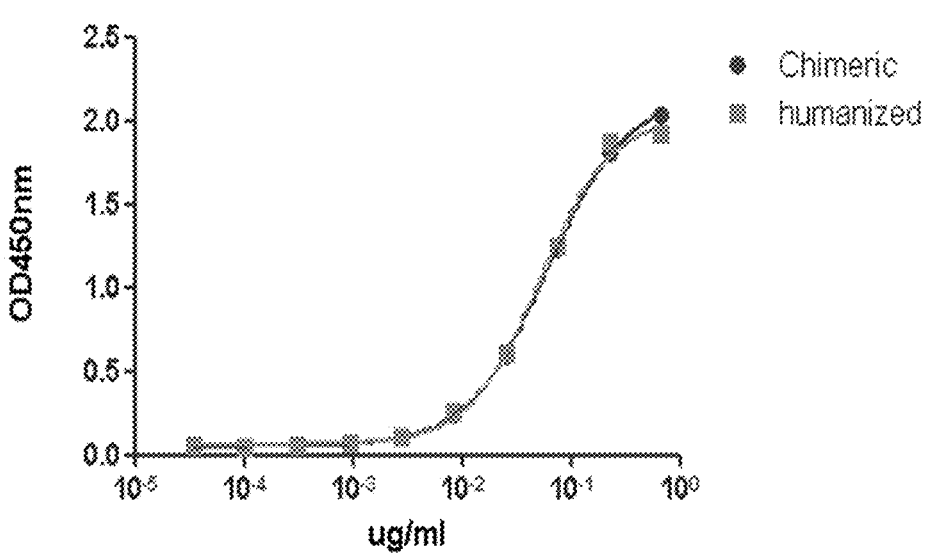
FIG. 8 shows a graph showing the binding curves of 4D3 humanized antibody and chimeric antibody at the same dilution concentration.

FIG. 8, EC50 (4D3-chimeric): 0.056 ug/ml; EC50 (4D3-humanized): 0.0502 ug/ml.

Example 15 Thermal Stability Analysis of 4D3 Humanized Antibody

The purified hum4D3 antibody was dialyzed, dialyzed with PBS buffer and calibrated to a final concentration of 2 mg/ml, and divided into two batches of 70 ul/tube, 3 tubes in each batch. The two batches of samples were placed at 4° C. and 37° C., and the sample tubes were taken out according to the 0th day, the 7th day, and the 14th day. The samples were used for SEC analysis to evaluate the degradation and aggregation of antibodies.

Figure 9:
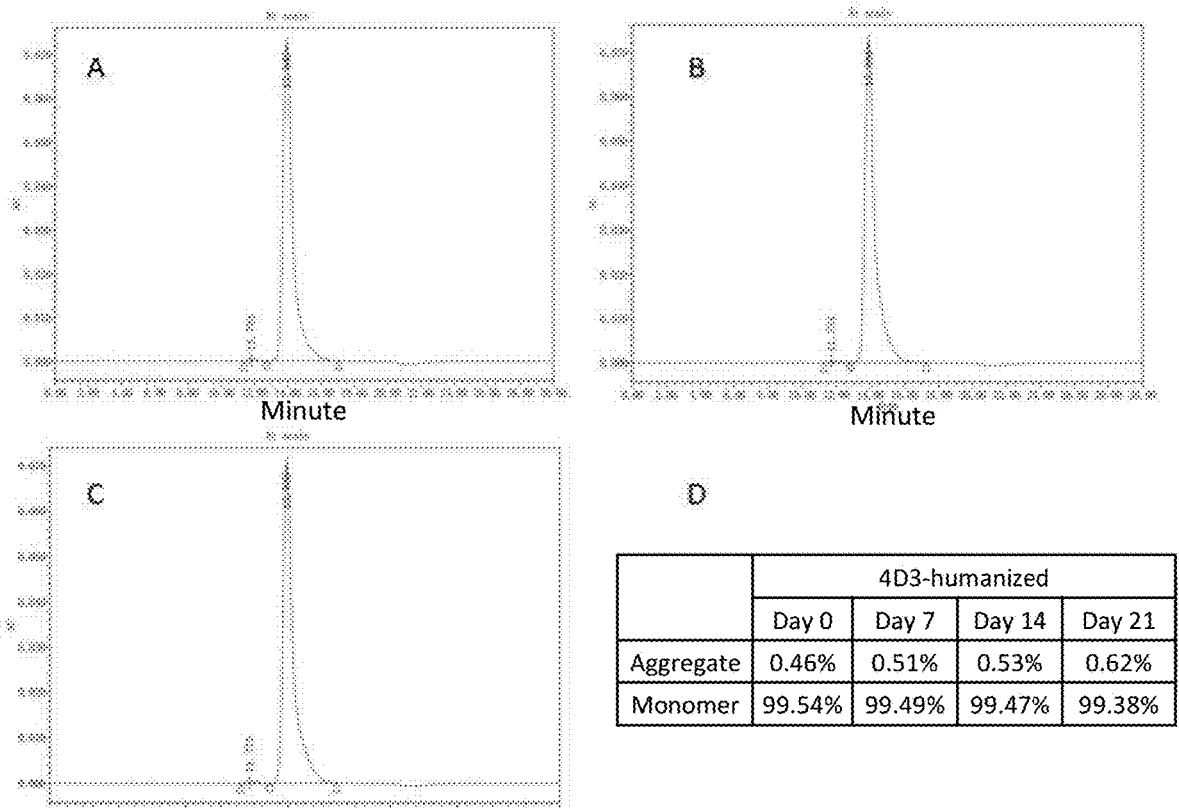
FIG. 9 shows a graph of the SEC detection results of the 4D3 humanized antibody on Day7 (A), Day14 (B), and Day21 (C)

FIG. 9: SEC detection results of the humanized 4D3 antibody on Day 7 (Figure A), Day 14 (Figure B), and Day 21 (Figure C). The monomers and aggregates of the 4D3-humanized antibody at each time point under the condition of 37° C., and the proportion (%) of the detection molecules in the 4D3-humanized antibody are shown in the table in Figure D.

Figure 10:
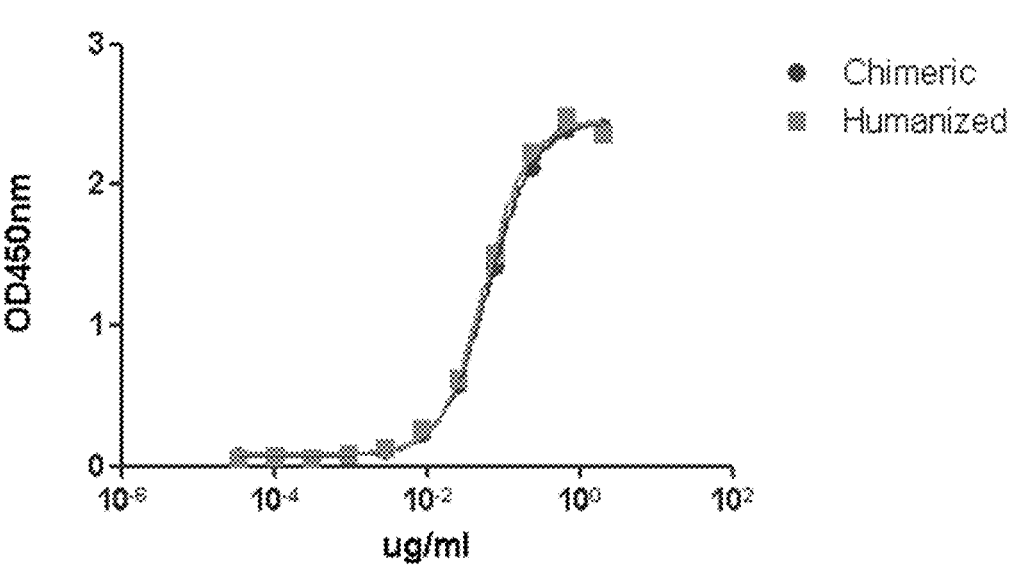
FIG. 10 shows a graph showing the binding curves of 7F11 humanized antibody and chimeric antibody at the same dilution concentration.

Example 16 Analysis of Relative Affinity and Binding Epitope Consistency of 7F11 Humanized Antibody Refer to the operating procedure in Embodiment 14 to evaluate the relative affinity of the 7F11 humanized antibody FIG. 10: Binding curve of 7F11 humanized antibody and chimeric antibody at the same dilution concentration, EC50 (7F11-chimeric): 0.061ug/ml; EC50 (7F11-humanized): 0.0601ug/ml.

Example 17 Thermal Stability Analysis of 7F11 Humanized Antibody

The thermal stability analysis of the 7F11 humanized antibody was performed in reference to the operation procedure in Embodiment 15.

Figure 11:
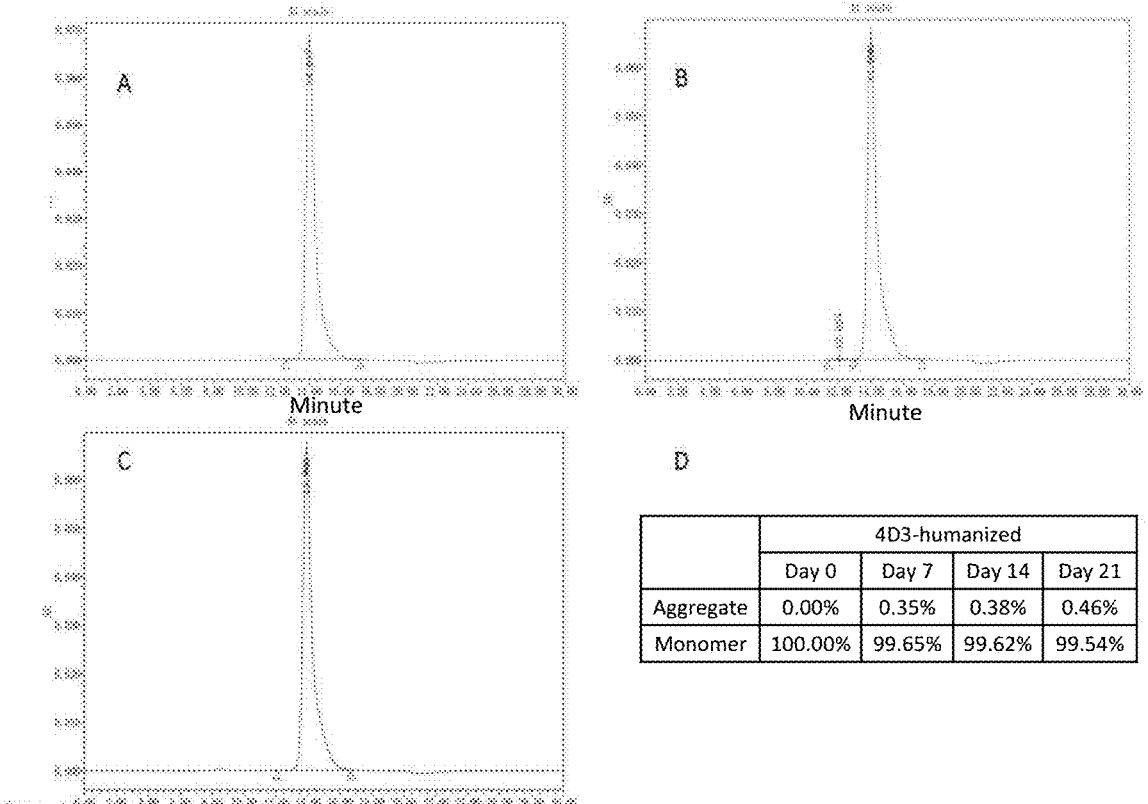
FIG. 11 shows a graph of the SEC detection results of the 7F11 humanized antibody on Day 7 (A), Day 14 (B), and Day 21 (C)

FIG. 11 shows SEC detection results of the 7F11 humanized antibody on Day7 (Figure A), Day14 (Figure B) and Day21 (Figure C). The monomers and aggregates of the 7F11-humanized antibody at each time point under the condition of 37° C., and the proportion (%) of the detection molecules in the 7F11-humanized antibody are shown in the table in Figure D.

Example 18 Antigen Affinity Analysis of Humanized Antibody and Parent Antibody Pall ForteBio Octet optical analysis technology platform is used to evaluate the absolute affinity of antibody-antigen binding. In this method, the biotin-labeled antigen is immobilized on the surface of the streptavidin biosensor chip, the baseline is balanced for 180 seconds, and then it binds with the antibody diluted in the solution concentration gradient for 30 seconds, which increases the optical thickness of the chip, resulting in The wavelength shifts ($\Delta\lambda$), and then enters the dissociation phase of 30 sec. The interaction between the Trop2 antigen and the corresponding antibody is measured in real time, and the specificity of binding, binding rate, dissociation rate or sample concentration are precisely and accurately measured at each concentration. After summarizing the k-on and k-off values under at least 5 concentration gradients, the KD binding constant is obtained.

| Ab Code | KD (M) | ka (1/Ms) | kd (1/s) | $R^2$ |
|---------|--------|-----------|----------|-------|
| ch4D3 | 6.89E−09 | 2.35E+05 | 1.62E−03 | 0.9935 |
| Hu4D3 | 3.07E−08 | 1.39E+05 | 4.28E−03 | 0.9916 |
| ch7F11 | 6.11E−11 | 2.43E+05 | 1.45E−05 | 0.9925 |
| Hu7F11 | 9.94E−11 | 1.86E+05 | 1.85E−05 | 0.9966 |

Example 19 Activity Analysis and Binding Epitope Consistency Analysis of 4D3 Humanized Antibody and Chimeric Antibody The 4D3-humanized antibody was labeled with biotin, and the inflection point value of the binding curve was determined by ELISA to be 0.5 ng/ml. Prepare an ELISA blocking solution containing 0.5 ng/ml 4D3 biotin-labeled antibody, and configure 50 ug/ml of competing antibodies 4D3-chimeric and 4D3-humanized on the basis of this solution. Add the solution containing biotin-labeled antibody and competing antibody to A1~A12, 150 ul per well, then aspirate 50 ul and add to B2~B12, mix well with the pre-added biotin antibody solution with a volume of 100 ul, and then dilute 3 times in sequence To H1~H12, incubate at 37° C. for 1 hr, then wash and incubate the anti-human IgG Fc secondary antibody, incubate at 37° C. for 1 hr, then wash 3 times, perform color development for 25 min and read the value.

Figure 12:
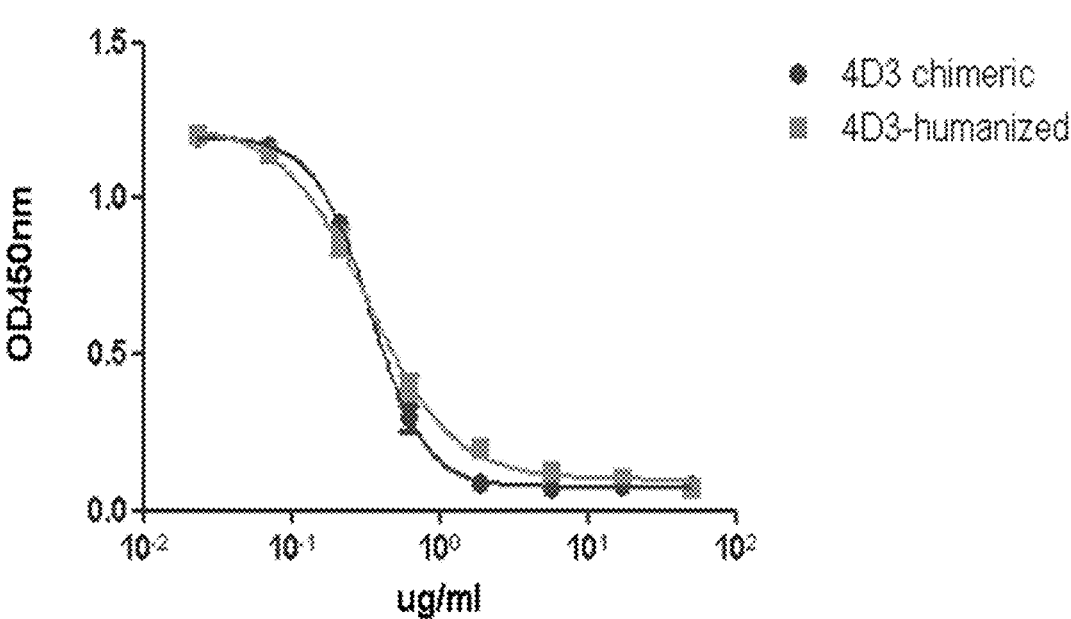
FIG. 12 shows a graph showing results of binding competition between 4D3-humanized-biotin antibody and hu4D3 antibody to 0.02-50 ug/ml ch4D3.

FIG. 12: 4D3-humanized-biotin antibodies compete with ch4D3 and hum4D3 antibodies at 0.02-50ug/ml, respectively. The two competing antibodies show the same degree of competitive activity and bind to the same epitope. EC50 (ch4D3): 0.336ug/ml. EC50(hum4D3): 0.326ug/ml Example 20 Activity Analysis and Binding Epitope Consistency Analysis of 7F11 Humanized Antibody, Humanized Antibody, and Chimeric Antibody With reference to the operating procedure in Embodiment 19, the epitope competition activity and binding epitope consistency of 7F11 were analyzed.

Figure 13:
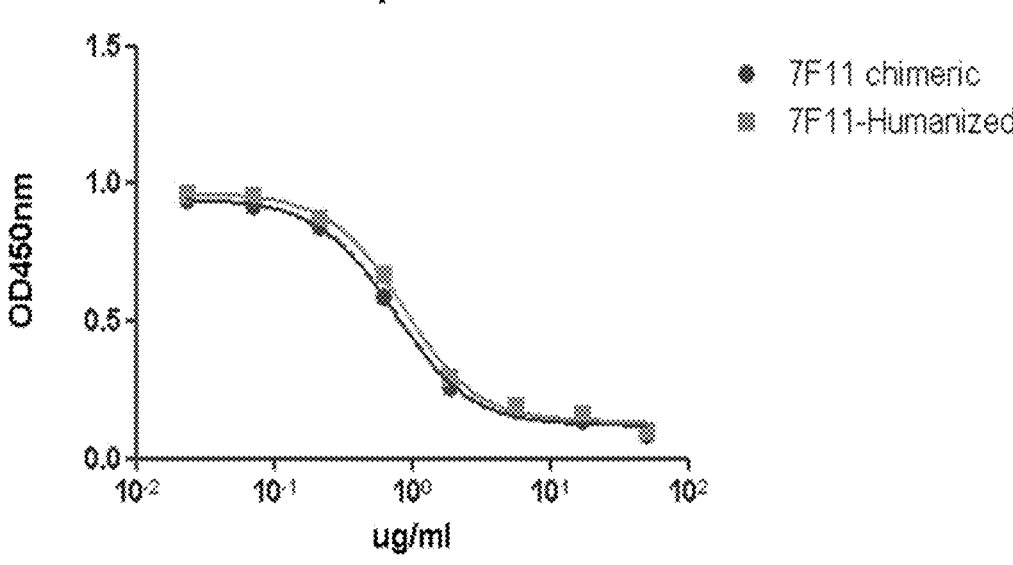
FIG. 13 shows a graph showing results of binding competition between 7F11-humanized-biotin antibody and hu7F11 antibody to 0.02-50ug/ml ch7F11.
Figure 14:
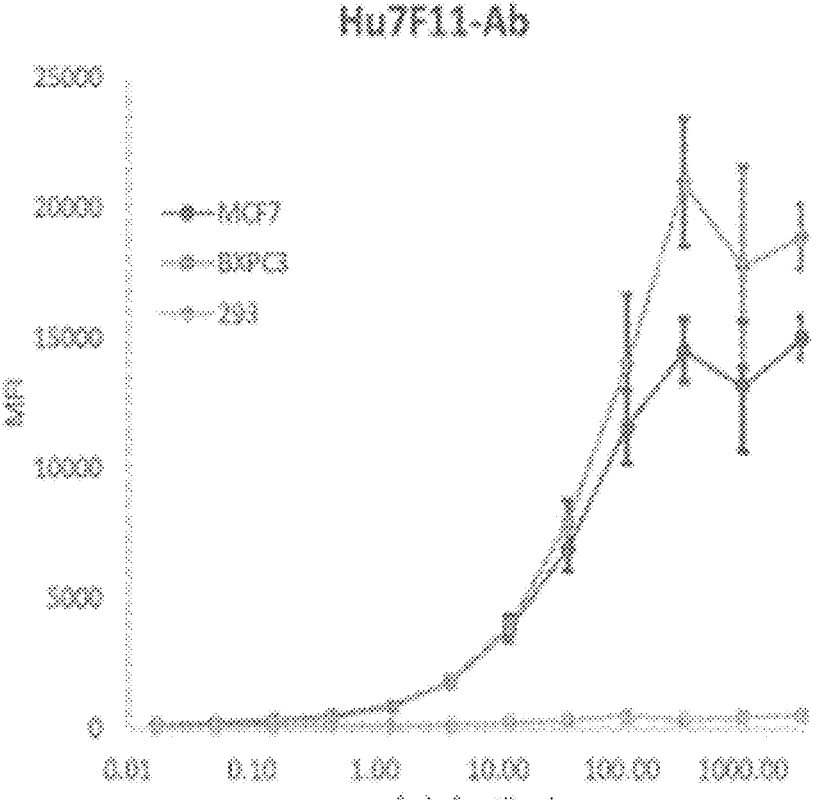
FIG. 14 shows binding data of hu7F11 antibody in three types of cells.
Figure 15:
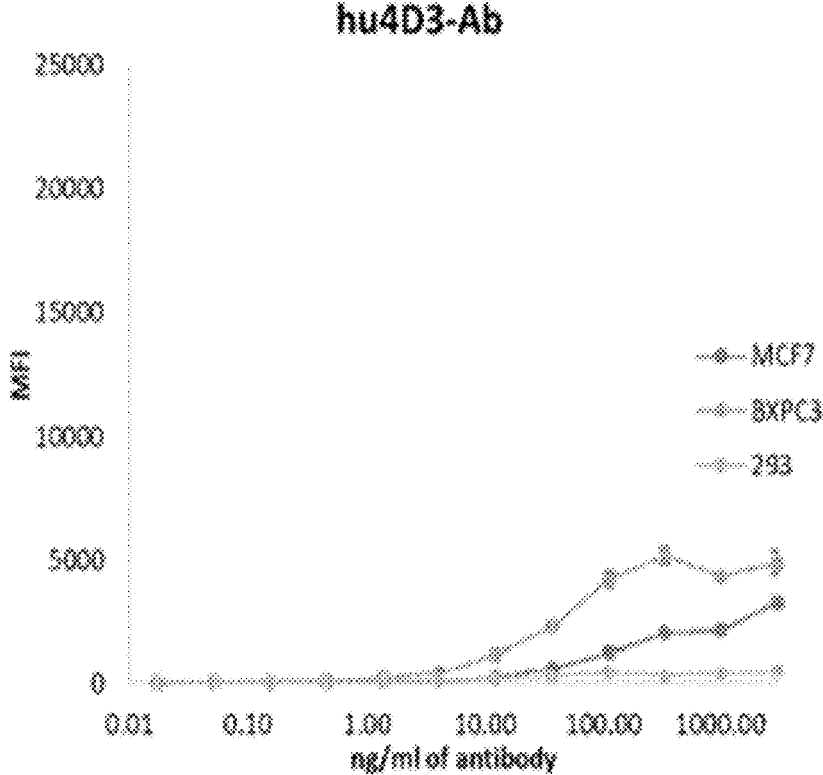
FIG. 15 shows binding data of Hu4D3 antibody in 3 types of cells.
Figure 16:
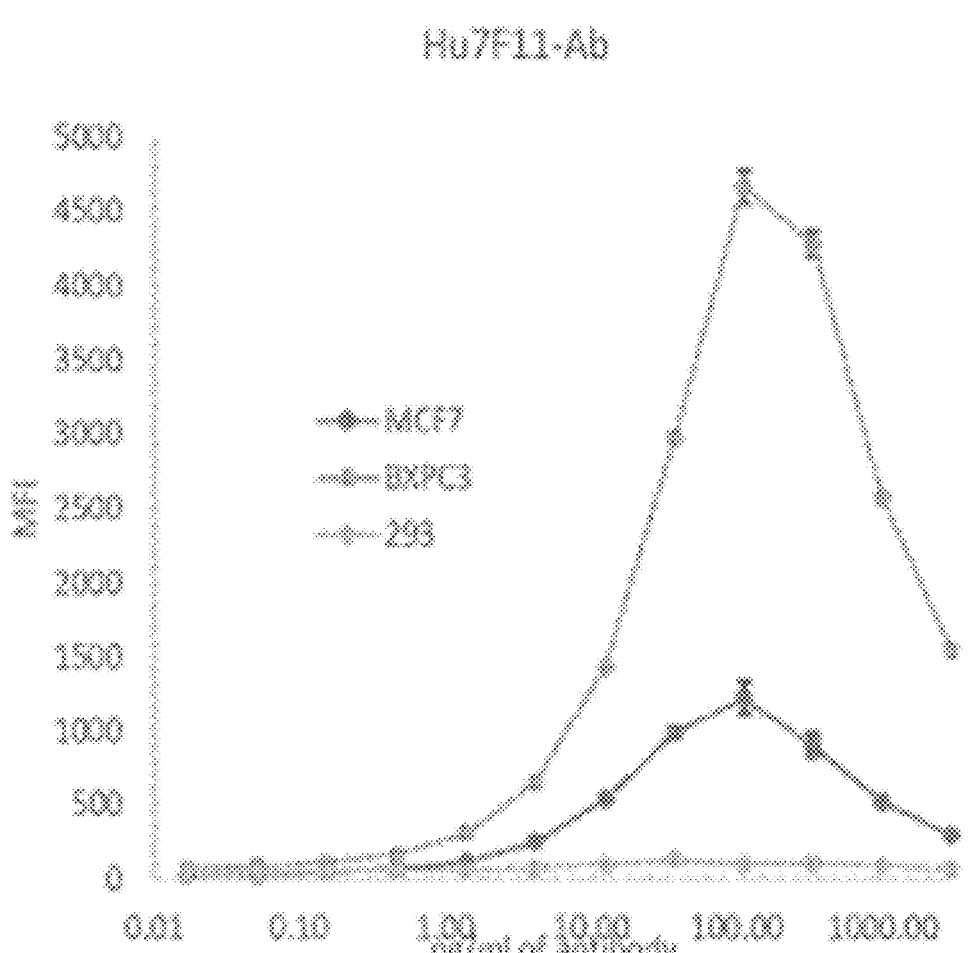
FIG. 16 shows endocytosis data of the hu7F11 antibody in three types of cells.
Figure 17:
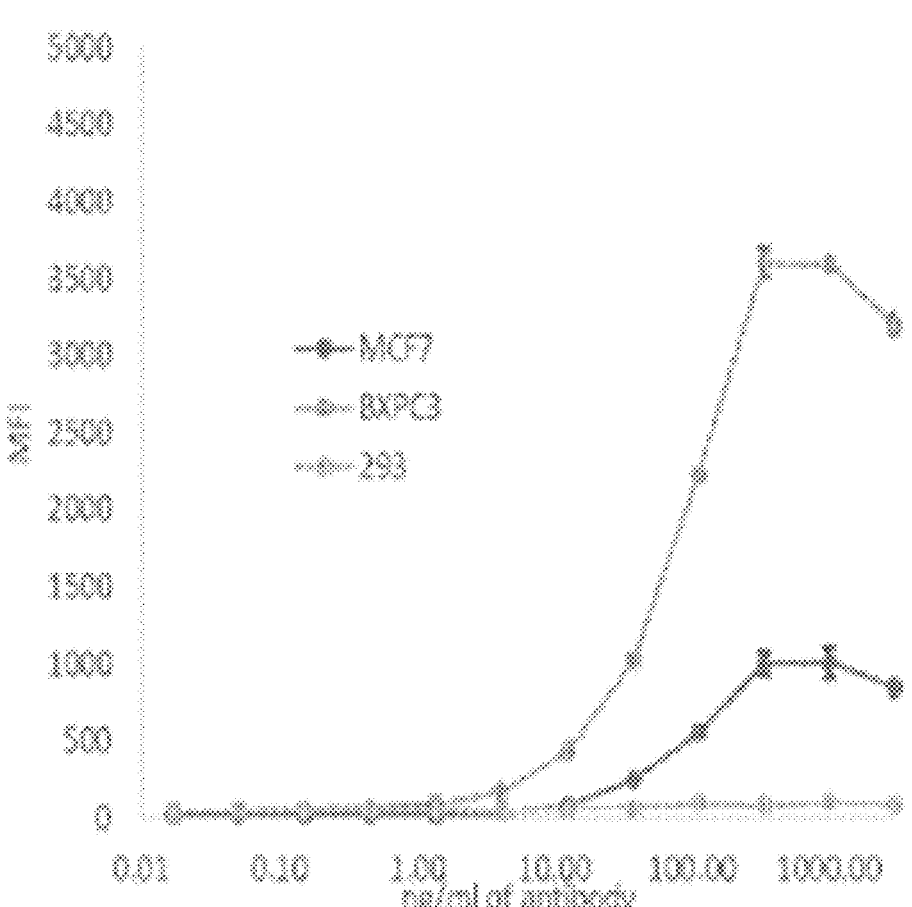
FIG. 17 shows endocytosis data of Hu4D3 antibody in three types of cells.

FIG. 13: The 7F11-humanized-biotin antibody competes with 0.02-50ug/ml ch7F11 and hum7F11 antibodies, respectively. The two competing antibodies show the same degree of competitive activity and bind the same epitope. EC50 (ch7F11): 0.732ug/ml. EC50 (hum7F11): 0.856ug/ml.

Example 21 Cell Binding and Endocytosis of the Humanized Antibody hu7F11 and hu4D3

Use HEK293 cells as negative cells and BXPC-3 and MCF-7 cells as positive cells to test the binding and endocytosis of each antibody at gradient concentrations. For cell binding test, bind for 1 hr at 4° C., then add conventional FITC-labeled fluorescent secondary antibody, and collect data by flow cytometry.

The endocytosis test uses the acid-sensitive small molecule dye Phrodo-Red goat anti-human secondary antibody, which is incubated with each concentration of the primary antibody to form a complex, and then incubated with each cell line for 16 hours. After sampling, at least 10,000 cells are laid in the cell wells of each 96-well plate, and the data is collected and analyzed by a flow cytometer. Count the average fluorescence intensity values of cells at various concentrations in the far-red light channel, and plot the degree of endocytosis curve with the antibody concentration as the abscissa.

Comparing the binding levels of hu7F11 and Hu4D3 antibodies in the three types of cells, BxPC-3 cells have the highest binding level. Comparison of the degree of endocytosis of hu7F11 and Hu4D3 antibodies in three types of cells. BxPC-3 cells have the highest level of endocytosis.

---

Sequence Listing

---

I. Amino Acid Sequence

---

1. CDR region:
SEQ ID No: 1 (4D3-CDRH1)
GYTFTSFD

SEQ ID No: 2 (4D3-CDRH2)
IFPGDGN

SEQ ID No: 3 (4D3-CDRH3)
VRGEALYYFDY

SEQ ID No: 4 (7F11-CDRH1)
GYTFTDHV

SEQ ID No: 5 (7F11-CDRH2)
IYPGSDNS

SEQ ID No: 6 (7F11-CDRH3)
AREGYGYGKNGVGYAMDY

SEQ ID No: 7 (4D3-CDRL1)
QDINKY

SEQ ID No: 8 (4D3-CDRL2)
STS

SEQ ID No: 9 (4D3-CDRL3)
LQYDDLFT

SEQ ID No: 10 (7F11-CDRL1)
QSVSND

SEQ ID No: 11 (7F11-CDRL2)
YAS

SEQ ID No: 12 (7F11-CDRL3)
QQDYSSPWT

2. Chimeric Antibodies:
SEQ ID No: 13 (4D3-H)
MGWSWVFLFLLSVTAGVHSQVQLQQSGAELVKPGASVKLSCKASGYTFTSFDINWVRQRPEQGLEWIGWIF
PGDGNTKSNEKFKGKATLTTDKSSSTAYMQLSRLTSEDSAVYFCVRGEALYYFDYWGPGTTLTVSSASTKGPSV
FPLAPSSKSTSGGTAALGCLVKDYFPEPVTVSWNSGALTSGVHTFPAVLQSSGLYSLSSVVTVPSSSLGTQTYICN
VNHKPSNTKVDKRVEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPVLDSDGSFFLYSKLTVDKSRWQQG
NVFSCSVMHEALHNHYTOKSLSLSPGK -continued

---

Sequence Listing

---

SEQ ID No: 14 (4D3-L)
MRPSIQFLGLLLFWLHGAQCDIQMTQSPSSLSASLGGKVTITCKPSQDINKYIAWYQHKPGKGPRLLIHSTSTL
QPGIPSRFSGSGSGRDYSFTISNLEPEDIATYYCLQYDDLFTFGSGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGLSSPV
TKSFNRGEC

SEQ ID No: 15 (7F11-H)
MEWRIFLFILSGTAGVHSQVQLQQSGPEVVKPGASVKMSCKASGYTFTDHVISWVKQRTGQGLEWIGQIYP
GSDNSYYSEKLKDKATLTADKSSNTAYMQLVSLTSEDSAVYFCAREGYGYGKNGVGYAMDYWGQGTSVTVSS
ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKRVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPPVLDSDGSFFLYSKLTV
DKSRWQQGNVFSCSVMHEALHNHYTQKSLSLSPGK

SEQ ID No: 16 (7F11-L)
MKSQTQVFVFLLLCVSGAHGSIVMTQTPKFLLVSAGDRVTITCKASQSVSNDVVWYQQKPGQSPKLLIYYASN
RYTGVPDRFTGSGYGTDFTFTISTAQAEDLAVYFCQQDYSSPWTFGGGTKLEIKRTVAAPSVFIFPPSDEQLKS
GTASVVCLLNNFYPREAKVQWKVDNALQSGNSQESVTEQDSKDSTYSLSSTLTLSKADYEKHKVYACEVTHQ
GLSSPVTKSFNRGEC

3. Humanized antibodies:
SEQ ID No: 17 (4D3-CDR-H)
MGWSWVFLFLLSVTAGVHSQVQLVQSGAEVKKPGASVKLSCKASGYTFTSFDINWVRQAPEQRLEWMGW
IFPGDGNTKYSQKFQGRATITRDTSASTAYMELSSLRSEDTAVYYCVRGEALYYFDYWGQGTLVTVSSASTKGP
SVFPLAPSSKSTSGGTAALGCLVKDYFPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTTPPVLDSDGSFFLYSKLTVDKSRWQ
QGNVFSCSVMHEALHNHYTQKSLSLSPG SEQ ID No: 18 (4D3-CDR-L)
MRPSIQFLGLLLFWLHGAQCDIQMTQSPSSLSASVGDRVTITCRASQDINKYLAWYQQKPGKVPKLLIYSTSTL
QSGVPSRFSGSGSGTDFTLTISSLQPEDVATYYCLQYDDLFTFGQGTKLEIKRTVAAPSVFIFPPSDEQLKSGTAS
VVCLLNNFYPREAKVQWKVDNALQSGNSQESVTEQDSKDSTYSLSSTLTLSKADYEKHKVYACEVTHQGLSSP
VTKSFNRGEC SEQ ID No: 19 (7F11-IMGT-H)
MEWRIFLFILSGTAGVHSQVQLVQSGAEVKKPGASVKVSCKASGYTFTDHVISWVRQATGQGLEWMGQIYP
GSDNSYYAQKFQGRVTLTADKSINTAYMELSSLRSEDTAVYYCAREGYGYGKNGVGYAMDYWGQGTLVTVSS
ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKRVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIEKTISKA
KGQPREPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPG SEQ ID No: 20 (7F11-IMGT-L)
MKSQTQVFVFLLLCVSGAHGDIVMTQSPDSLAVSLGERATINCKASQSVSNDVVWYQQKPGQPPKLLIYYAS
NRYTGVPDRFSGSGYGTDFTLTISSLQAEDVAVYYCQQDYSSPWTFGGGTKVEIKRTVAAPSVFIFPPSDEQLK
SGTASVVCLLNNFYPREAKVQWKVDNALQSGNSQESVTEQDSKDSTYSLSSTLTLSKADYEKHKVYACEVTHQ
GLSSPVTKSFNRGEC

---

II. Nucleic Acid Sequence

---

1. CDR:
SEQ ID No: 21 (4D3-CDRH1)
GGCTACACCTTCACAAGCTTTGAT

SEQ ID No: 22 (4D3-CDRH2)
ATTTTTCCTGGAGATGGTAAT

SEQ ID No: 23 (4D3-CDRH3)
GTAAGAGGGGAGGCCCTGTATTACTTTGACTAC

SEQ ID No: 24 (7F11-CDRH1)
GGATACACATTCACTGACCATGTC

SEQ ID No: 25 (7F11-CDRH2)
ATTTATCCTGGAAGTGATAATAGT

SEQ ID No: 26 (7F11-CDRH3)
GCAAGAGAGGGCTATGGTTATGGAAAAAACGGAGTTGGCTATGCTATGGACTAC

Sequence Listing

SEQ ID No: 27 (4D3-CDRL1)
CAAGACATTAATAAGTAT

SEQ ID No: 28 (4D3-CDRL2)
TCCACATCT

SEQ ID No: 29 (4D3-CDRL3)
CTGCAGTATGATGATCTATTCACG

SEQ ID No: 30 (7F11-CDRL1)
CAGAGTGTGAGTAATGAT

SEQ ID No: 31 (7F11-CDRL2)
TATGCATCC

SEQ ID No: 32 (7F11-CDRL3)
CAGCAGGATTATTCCTCTCCGTGGACG

2. Chimeric antibodies:
SEQ ID No: 33 (4D3-H)
ATGGGATGGAGCTGGGTCTTTCTCTTCCTCCTGTCAGTAACTGCAGGTGTCCACTCCCAGGTTCAGCTGCA
GCAGTCTGGAGCTGAACTGGTAAAGCCTGGGGCTTCAGTGAAGTTGTCCTGCAAGGCTTCTGGCTACACC
TTCACAAGCTTTGATATAAACTGGGTGAGGCAGAGGCCTGAACAGGGACTTGAGTGGATTGGATGGATTT
TTCCTGGAGATGGTAATACTAAGTCCAATGAGAAATTTAAGGGCAAGGCCACACTGACTACAGACAAATCC
TCCAGCACAGCCTACATGCAGCTCAGCAGGCTGACATCTGAGGACTCTGCTGTCTATTTCTGTGTAAGAGG
GGAGGCCCTGTATTACTTTGACTACTGGGGCCCAGGCACCACTCTCACAGTCTCCTCAGCTAGCACCAAGG
GCCCATCGGTCTTCCCCCTGGCACCCTCCTCCAAGAGCACCTCTGGGGGCACAGCGGCCCTGGGCTGCCT
GGTCAAGGACTACTTCCCCGAACCGGTGACGGTGTCGTGGAACTCAGGCGCCCTGACCAGCGGCGTGCA
CACCTTCCCGGCTGTCCTACAGTCCTCAGGACTCTACTCCCTCAGCAGCGTGGTGACCGTGCCCTCCAGCA
GCTTGGGCACCCAGACCTACATCTGCAACGTGAATCACAAGCCCAGCAACACCAAGGTGGACAAGAGAG
TTGAGCCCAAATCTTGTGACAAAACTCACACATGCCCACCGTGCCCAGCACCTGAACTCCTGGGGGGACC
GTCAGTCTTCCTCTTCCCCCCAAAACCCAAGGACACCCTCATGGTCTCCCGGACCCCTGAGGTCACATGCG
TGGTGGTGGACGTGAGCCACGAAGACCCTGAGGTCAAGTTCAACTGGTACGTGGACGGCGTGGAGGTG
CATAATGCCAAGACAAAGCCGCGGGAGGAGCAGTACAACAGCACGTACCGTGTGGTCAGCGTCCTCACC
GTCCTGCACCAGGACTGGCTGAATGGCAAGGAGTACAAGTGCAAGGTCTCCAACAAAGCCCTCCCAGCC
CCCATCGAGAAAACCATCTCCAAAGCCAAAGGGCAGCCCCGAGAACCACAGGTGTACACCCTGCCCCCAT
CCCGGGAGGAGATGACCAAGAACCAGGTCAGCCTGACCTGCCTGGTCAAAGGCTTCTATCCCAGCGACAT
CGCCGTGGAGTGGGAGAGCAATGGGCAGCCGGAGAACAACTACAAGACCACGCCTCCCGTGCTGGACTC
CGACGGCTCCTTCTTCCTCTATAGCAAGCTCACCGTGGACAAGAGCAGGTGGCAGCAGGGGAACGTCTTC
TCATGCTCCGTGATGCATGAGGCTCTGCACAACCACTACACGCAGAAGAGCCTCTCCCTGTCTCCGGGTAA
ATGA SEQ ID No: 34 (4D3-L)
ATGAGACCGTCTATTCAGTTCCTGGGGCTCTTGTTGTTCTGGCTTCATGGTGCTCAGTGTGACATCCAGATG
ACACAGTCTCCATCCTCACTGTCTGCATCTCTGGGAGGCAAAGTCACCATCACTTGCAAGCCAAGCCAAGA
CATTAATAAGTATATAGCTTGGTACCAACACAAGCCTGGAAAAGGTCCTAGGCTGCTCATACATTCCACATCT
ACATTACAGCCAGGCATCCCATCAAGGTTCAGTGGAAGTGGGTCTGGGAGAGATTATTCCTTCACCATCAG
CAACCTGGAACCTGAAGATATTGCAACTTATTATTGTCTGCAGTATGATGATCTATTCACGTTCGGCTCGGG
GACAAAGTTGGAAATAAAACGTACGGTGGCTGCACCATCTGTCTTCATCTTCCCGCCATCTGATGAGCAGT
TGAAATCTGGAACTGCCTCTGTTGTGTGCCTGCTGAATAACTTCTATCCCAGAGAGGCCAAAGTACAGTGG
AAGGTGGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTACGCCTGCG
AAGTCACCCATCAGGGCCTGAGCTCGCCCGTCACAAAGAGCTTCAACAGGGGAGAGTGTTAG SEQ ID No: 35 (7F11-H)
ATGGAATGGAGGATCTTTCTCTTCATCCTGTCAGGAACTGCAGGTGTCCACTCCCAGGTTCAGCTGCAGCA
GTCTGGACCTGAGGTGGTGAAGCCTGGGGCTTCAGTGAAGATGTCCTGCAAGGCTTCTGGATACACATTC
ACTGACCATGTCATAAGCTGGGTGAAGCAGAGAACTGGACAGGGCCTTGAGTGGATTGGACAGATTTATC
CTGGAAGTGATAATAGTTACTACAGTGAGAAGTTGAAGGACAAGGCCACACTGACTGCAGACAAATCCTC
CAACACAGCCTACATGCAGCTCGTCAGCCTGACATCTGAGGACTCTGCGGTCTATTTCTGTGCAAGAGAGG
GCTATGGTTATGGAAAAAACGGAGTTGGCTATGCTATGGACTACTGGGGTCAAGGAACCTCAGTCACCGTC
TCCTCAGCTAGCACCAAGGGCCCATCGGTCTTCCCCCTGGCACCCTCCTCCAAGAGCACCTCTGGGGGACA
CAGCGGCCCTGGGCTGCCTGGTCAAGGACTACTTCCCCGAACCGGTGACGGTGTCGTGGAACTCAGGCG
CCCTGACCAGCGGCGTGCACACCTTCCCGGCTGTCCTACAGTCCTCAGGACTCTACTCCCTCAGCAGCGTG
GTGACCGTGCCCTCCAGCAGCTTGGGCACCCAGACCTACATCTGCAACGTGAATCACAAGCCCAGCAACA
CCAAGGTGGACAAGAGAGTTGAGCCCAAATCTTGTGACAAAACTCACACATGCCCACCGTGCCCAGCACC
TGAACTCCTGGGGGGACCGTCAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAGGTCAAGTTCAACTGGTACG
TGGACGGCGTGGAGGTGCATAATGCCAAGACAAAGCCGCGGGAGGAGCAGTACAACAGCACGTACCGT
GTGGTCAGCGTCCTCACCGTCCTGCACCAGGACTGGCTGAATGGCAAGGAGTACAAGTGCAAGGTCTCCA
ACAAAGCCCTCCCAGCCCCCATCGAGAAAACCATCTCCAAAGCCAAAGGGCAGCCCCGAGAACCACAGG
TGTACACCCTGCCCCCATCCCGGGAGGAGATGACCAAGAACCAGGTCAGCCTGACCTGCCTGGTCAAAGG
CTTCTATCCCAGCGACATCGCCGTGGAGTGGGAGAGCAATGGGCAGCCGGAGAACAACTACAAGACCAC
GCCTCCCGTGCTGGACTCCGACGGCTCCTTCTTCCTCTATAGCAAGCTCACCGTGGACAAGAGCAGGTGG
CAGCAGGGGAACGTCTTCTCATGCTCCGTGATGCATGAGGCTCTGCACAACCACTACACGCAGAAGAGCC
TCTCCCTGTCTCCGGGTAAATGA Sequence Listing SEQ ID No: 36 (7F11-L)
ATGAAGTCACAGACCCAGGTCTTCGTATTTCTACTGCTCTGTGTGTCTGGTGCTCATGGGAGTATTGTGATG
ACCCAGACTCCCAAATTCCTGCTTGTATCAGCAGGAGACAGGGTTACCATAACCTGCAAGGCCAGTCAGA
GTGTGAGTAATGATGTAGTTTGGTACCAACAGAAGCCAGGGCAGTCTCCTAAACTGCTGATATACTATGCAT
CCAATCGCTACACTGGAGTCCCTGATCGCTTCACCGGCAGTGGATATGGGACGGATTTCACTTTCACCATCA
GCACTGCGCAGGCTGAAGACCTGGCAGTTTATTTCTGTCAGCAGGATTATTCCTCTCCGTGGACGTTCGGT
GGGGGCACCAAGCTGGAAATCAAACGTACGGTGGCTGCACCATCTGTCTTCATCTTCCCGCCATCTGATGA
GCAGTTGAAATCTGGAACTGCCTCTGTTGTGTGCCTGCTGAATAACTTCTATCCCAGAGAGGCCAAAGTAC
AGTGGAAGGTGGATAACGCCCTCCAATCGGGTAACTCCCAGGAGAGTGTCACAGAGCAGGACAGCAAGG
ACAGCACCTACAGCCTCAGCAGCACCCTGACGCTGAGCAAAGCAGACTACGAGAAACACAAAGTCTACG
CCTGCGAAGTCACCCATCAGGGCCTGAGCTCGCCCGTCACAAAGAGCTTCAACAGGGGAGAGTGTTAG 3. Humanized antibodies:
SEQ ID No: 37 (4D3-CDR-H)
ATGGGCTGGTCCTGGGTGTTCCTGTTCCTGCTGAGCGTGACCGCCGGCGTGCACTCCCAGGTGCAGCTGG
TGCAGTCCGGCGCCGAGGTGAAGAAGCCCGGCGCCTCCGTGAAGCTGAGCTGTAAGGCCTCCGGCTACA
CCTTCACCTCCTTCGACATTAACTGGGTGCGGCAGGCCCCCGAGCAGCGCCTGGAGTGGATGGGCTGGAT
CTTCCCCGGCGACGGCAACACCAAGTACTCCCAGAAGTTCCAGGGAAGAGCTACCATCACCAGAGATACA
TCCGCTTCTACAGCTTACATGGAGCTGTCTAGCCTGAGATCTGAGGATACAGCTGTGTATTACTGTGTGAGA
GGAGAGAGGCTCTGTACTATTTTGATTATTGGGGCCAGGGCACCCTGGTGACAGTGTCTTCTGCTAGCACCAA
GGGCCCATCGGTCTTCCCCCTGGCACCCTCCTCCAAGAGCACCTCTGGGGGCACAGCGGCCCTGGGCTGC
CTGGTCAAGGACTACTTCCCCGAACCGGTGACGGTGTCGTGGAACTCAGGCGCCCTGACCAGCGGCGTG
CACACCTTCCCGGCTGTCCTACAGTCCTCAGGACTCTACTCCCTCAGCAGCGTGGTGACCGTGCCCTCCAG
CAGCTTGGGCACCCAGACCTACATCTGCAACGTGAATCACAAGCCCAGCAACACCAAGGTGGACAAGAGAG
AGTTGAGCCCAAATCTTGTGACAAAACTCACACATGCCCACCGTGCCCAGCACCTGAACTCCTGGGGGGA
CCGTCAGTCTTCCTCTTCCCCCCAAAACCCAAGGACACCCTCATGATCTCCCGGACCCCTGAGGTCACATGC
GTGGTGGTGGACGTGAGCCACGAAGACCCTGAGGTCAAGTTCAACTGGTACGTGGACGGCGTGGAGGT
GCATAATGCCAAGACAAAGCCGCGGGAGGAGCAGTACAACAGCACGTACCGTGTGGTCAGCGTCCTCAC
CGTCCTGCACCAGGACTGGCTGAATGGCAAGGAGTACAAGTGCAAGGTCTCCAACAAAGCCCTCCCAGC
CCCCATCGAGAAAACCATCTCCAAAGCCAAAGGGCAGCCCCGAGAACCACAGGTGTACACCCTGCCCCCA
TCCCGGGATGAGCTGACCAAGAACCAGGTCAGCCTGACCTGCCTGGTCAAAGGCTTCTATCCCAGCGACA
TCGCCGTGGAGTGGGAGAGCAATGGGCAGCCGGAGAACAACTACAAGACCACGCCTCCCGTGCTGGACT
CCGACGGCTCCTTCTTCCTCTATAGCAAGCTCACCGTGGACAAGAGCAGGTGGCAGCAGGGGAACGTCTT
CTCATGCTCCGTGATGCATGAGGCTCTGCACAACCACTACACGCAGAAGAGCCTCTCCCTGTCTCCGGGTT
AA SEQ ID No: 38 (4D3-CDR-L)
ATGAGACCTTCTATLLAGTTTCTGGGCCTGCTGCTGTTTTGGCTGCATGGCGCCCAGTGCGATATCCAGATG
ACCCAGTCTCCATCTAGCCTGTCCGCTTCTGTGGGCGATAGAGTGACCATCACATGCAGAGCTTCTCAGGA
TATCAATAAGTATCTGGCTTGGTATCAGCAGAAGCCTGGAAAGGTGCCTAAGCTGCTGATCTACTCTACATC
TACCCTGCAGTCTGGAGTGCCTTCTAGATTTTCTGGATCTGGCTCTGGCACCGATTTTACACTGACAATCTC
TTCTCTGCAGCCTGAGGATGTGGCTACATATTATTGTCTGCAGTATGATGATCTGTTCACCTTTGGCCAGGG
CACCAAGCTGGAGATCAAGCGTACGGTGGCTGCACCATCTGTCTTCATCTTCCCGCCATCTGATGAGCAGT
TGAAATCTGGAACTGCCTCTGTTGTGTGCCTGCTGAATAACTTCTATCCCAGAGAGGCCAAAGTACAGTGG
AAGGTGGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTACGCCTGCG
AAGTCACCCATCAGGGCCTGAGCTCGCCCGTCACAAAGAGCTTCAACAGGGGAGAGTGTTAG SEQ ID No: 39 (7F11-IMGT-H)
ATGGAGTGGAGAATCTTTCTGTTTATCCTGTCTGGCACAGCTGGAGTGCATTCTCAGGTGCAGCTGGTGCA
GTCTGGGGCCGAGGTGAAAAAGCCAGGCGCTTCTGTGAAGGTGTCTTGCAAGGCCTCCGGCTACACCTT
CACCGACCACGTGATCTCCTGGGTGCGCCAGGCCACCGGCCAGGGCCTGGAGTGGATGGGCCAGATCTA
CCCCGGCTCCGACAACTCCTACTACGCCCAGAAGTTCCAGGGCAGGGTGACTCTGACCGCCGACAAGTCC
ATCAACACCGCCTACATGGAGCTGTCCTCCCTGAGGTCCGAGGACACCGCCGTGTACTACTGCGCCAGGG
AGGGCTACGGCTACGGCAAGAACGGCGTGGGCTACGCCATGGATTATTGGGGCCAGGGCACCCTGGTGA
CAGTGTCTTCTGCTAGCACCAAGGGCCCATCGGTCTTCCCCCTGGCACCCTCCTCCAAGAGCACCTCTGGG
GGCACAGCGGCCCTGGGCTGCCTGGTCAAGGACTACTTCCCCGAACCGGTGACGGTGTCGTGGAACTCA
GGCGCCCTGACCAGCGGCGTGCACACCTTCCCGGCTGTCCTACAGTCCTCAGGACTCTACTCCCTCAGCAG
CGTGGTGACCGTGCCCTCCAGCAGCTTGGGCACCCAGACCTACATCTGCAACGTGAATCACAAGCCCAGC
AACACCAAGGTGGACAAGAGAGTTGAGCCCAAATCTTGTGACAAAACTCACACATGCCCACCGTGCCCAG
CACCTGAACTCCTGGGGGGACCGTCAGTCTTCCTCTTCCCCCCAAAACCCAAGGACACCCTCATGATCTCC
CGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCGCGGGAGGAGCAGTACAACAGCACGTAC
CGTGTGGTCAGCGTCCTCACCGTCCTGCACCAGGACTGGCTGAATGGCAAGGAGTACAAGTGCAAGGTCT
CCAACAAAGCCCTCCCAGCCCCCATCGAGAAAACCATCTCCAAAGCCAAAGGGCAGCCCCGAGAACCAC
AGGTGTACACCCTGCCCCCATCCCGGGATGAGCTGACCAAGAACCAGGTCAGCCTGACCTGCCTGGTCAA
AGGCTTCTATCCCAGCGACATCGCCGTGGAGTGGGAGAGCAATGGGCAGCCGGAGAACAACTACAAGAC
CACGCCTCCCGTGCTGGACTCCGACGGCTCCTTCTTCCTCTATAGCAAGCTCACCGTGGACAAGAGCAGGT
GGCAGCAGGGGAACGTCTTCTCATGCTCCGTGATGCATGAGGCTCTGCACAACCACTACACGCAGAAGAG
CCTCTCCCTGTCTCCGGGTTAA SEQ ID No: 40 (7F11-IMGT-L)
ATGAAGTCTCAGACCCAGGTGTTTGTGTTTCTGCTGCTGTGTGTGTCTGGCGCTCATGGCGATATCGTGATG
ACACAGTCTCCTGATTCTCTGGCCGTGTCTCTGGGCGAAAGAGCTACAATCAACTGTAAGGCTTCTCAGTC
TGTGTCTAATGATGTGGTGTGGTACCAGCAGAAGCCTGGGCAGCCCCCCAAGCTGCTGATCTACTACGCCT
CCAACAGGTACACCGGCGTGCCCGACAGGTTCTCCGGCTCCGGCTACGGCACCGACTTCACCCTGACCAT
CTCCTCCCTGCAGGCCGAGGACGTGGCCGTGTACTACTGCCAGCAGGACTACTCCTCCCCCTGGACCTTCG -continued

---

Sequence Listing

---

GCGGCGGCACCAAGGTGGAGATCAAGCGTACGGTGGCTGCACCATCTGTCTTCATCTTCCCGCCATCTGAT
GAGCAGTTGAAATCTGGAACTGCCTCTGTTGTGTGCCTGCTGAATAACTTCTATCCCAGAGAGGCCAAAGT
ACAGTGGAAGGTGGATAACGCCCTCCAATCGGGTAACTCCCAGGAGAGTGTCACAGAGCAGGACAGCAA
GGACAGCACCTACAGCCTCAGCAGCACCCTGACGCTGAGCAAAGCAGACTACGAGAAACACAAAGTCTA
CGCCTGCGAAGTCACCCATCAGGGCCTGAGCTCGCCCGTCACAAAGAGCTTCAACAGGGGAGAGTGTTA
G

---

What is claimed is:

1. An anti-TROP2 antibody or its Fv, scFv, Fab, F(ab')2, Fab', or scFv-Fc fragment thereof, comprising a heavy chain and a light chain, wherein the heavy chain comprises amino acid sequence SEQ ID NO: 13 or 17 and the light chain comprises amino acid sequence SEQ ID NO: 14 or 18, or wherein the heavy chain comprises amino acid sequence SEQ ID NO: 15 or 19 and the light chain comprises amino acid sequence SEQ ID NO: 16 or 20.

2. The antibody or its Fv, scFv, Fab, F(ab')2, Fab', or scFv-Fc fragment of claim 1, wherein the heavy chain comprises amino acid sequence SEQ ID NO: 17 and the light chain comprises amino acid sequence SEQ ID NO: 18, or wherein the heavy chain comprises amino acid sequence SEQ ID NO: 19 and the light chain comprises amino acid sequence SEQ ID NO: 20.

3. The antibody or its Fv, scFv, Fab, F(ab')2, Fab', or scFv-Fc fragment of claim 1, wherein the antibody or its Fv, scFv, Fab, F(ab')2, Fab', or scFv-Fc fragment is a monoclonal antibody or a derivative thereof.

4. The antibody or its Fv, scFv, Fab, F(ab')2, Fab', or scFv-Fc fragment of claim 1, wherein the antibody or its Fv, scFv, Fab, F(ab')2, Fab', or scFv-Fc fragment is of murine origin.

5. The antibody or its Fv, scFv, Fab, F(ab')2, Fab', or scFv-Fc fragment of claim 1, wherein the heavy chain comprises CDRH1, CDRH2, and CDRH3 from SEQ ID NO: 1, 2, and 3, respectively or CDRH1, CDRH2, and CDRH3 from SEQ ID NO: 4, 5, and 6 respectively.

6. An antibody fragment or its derivative having at least one of the following sets of CDRs wherein each set of CDRs comprises an amino acid sequence of SEQ ID NO: 4-6, 7-9, or 10-12.

7. The antibody or its Fv, scFv, Fab, F(ab')2, Fab', scFv-Fc fragments of claim 2, wherein the antibody or its Fv, scFv, Fab, F(ab')2, Fab', scFv-Fc fragments comprise humanized sequences.

8. The antibody or its Fv, scFv, Fab, F(ab')2, Fab', or scFv-Fc fragment of claim 5, wherein the light chain comprises CDRL1, CDRL2, and CDRL3 from SEQ ID NO: 7, 8, and 9 or CDRL1, CDRL2, and CDRL3 from SEQ ID NO: 10, 11, and 12.

9. A nucleic acid sequence, comprising the nucleic acid sequence encoding the antibody or its Fv, scFv, Fab, F(ab')2, Fab', scFv-Fc fragment of claim 1.

10. The isolated nucleic acid sequence of claim 9, comprising the nucleic acid sequence encoding the heavy chain having SEQ ID NO: 21, 22 and 23, or SEQ ID NO: 24, 25 and 26, and the nucleic acid sequence encoding the light chain having SEQ ID NO: 27, 28, and 29 or SEQ ID NO: 30, 31, and 32.

11. The nucleic acid sequence according to claim 10, comprising the nucleic acid sequence having SEQ ID NO: 33 and 34, or SEQ ID NO: 35 and 36.

12. The nucleic acid according to claim 10, comprising the nucleic acid sequence having SEQ ID NO: 37 and 38, or SEQ ID NO: 39 and 40.

13. An RNA, wherein the RNA sequence corresponds or is complementary to the nucleic acid sequences in claim 9.

14. An expression vector, comprising the nucleic acid sequences of claim 9.

15. A host, comprising the expression vector of claim 14.

16. The expression vector of claim 14 or the host of claim 15, wherein the expression vector or the host is configured to produce the amino acid sequence SEQ ID NO: 13, 14, 15 or 16.

17. A method for diagnosis or treating TROP2-related malignant tumors in a subject, comprising administering to the subject the antibody or its Fv, scFv, Fab, F(ab')2, Fab', scFv-Fc fragment of claim 1.

18. An immune-conjugate, comprising the antibody or its Fv, scFv, Fab, F(ab')2, Fab', scFv-Fc fragment of claim 1 and a cytotoxic compound or a radioactive element.

19. The immuno-conjugate of claim 18, wherein the cytotoxic compound comprises an alkylating agent, an anti-metabolite, an anti-tumor drug, a mitotic inhibitor, a chromatin function inhibitor, an anti-angiogenesis agent, an anti-androgen, an anti-estrogen, an immunomodulator, or a combination thereof.

* * * * *

SEQUENCE LISTING

<160> NUMBER OF SEQ ID NOS: 40

<210> SEQ ID NO 1
<211> LENGTH: 8
<212> TYPE: PRT
<213> ORGANISM: Artificial Sequence
<220> FEATURE:
<223> OTHER INFORMATION: synthesized

<400> SEQUENCE: 1

Gly Tyr Thr Phe Thr Ser Phe Asp
1               5

<210> SEQ ID NO 2
<211> LENGTH: 7
<212> TYPE: PRT
<213> ORGANISM: Artificial Sequence
<220> FEATURE:
<223> OTHER INFORMATION: synthesized

<400> SEQUENCE: 2

Ile Phe Pro Gly Asp Gly Asn
1               5

<210> SEQ ID NO 3
<211> LENGTH: 11
<212> TYPE: PRT
<213> ORGANISM: Artificial Sequence
<220> FEATURE:
<223> OTHER INFORMATION: synthesized

<400> SEQUENCE: 3

Val Arg Gly Glu Ala Leu Tyr Tyr Phe Asp Tyr
1               5                   10

<210> SEQ ID NO 4
<211> LENGTH: 8
<212> TYPE: PRT
<213> ORGANISM: Artificial Sequence
<220> FEATURE:
<223> OTHER INFORMATION: synthesized

<400> SEQUENCE: 4

Gly Tyr Thr Phe Thr Asp His Val
1               5

<210> SEQ ID NO 5
<211> LENGTH: 8
<212> TYPE: PRT
<213> ORGANISM: Artificial Sequence
<220> FEATURE:
<223> OTHER INFORMATION: synthesized

<400> SEQUENCE: 5

Ile Tyr Pro Gly Ser Asp Asn Ser

```
1               5

<210> SEQ ID NO 6
<211> LENGTH: 18
<212> TYPE: PRT
<213> ORGANISM: Artificial Sequence
<220> FEATURE:
<223> OTHER INFORMATION: synthesized

<400> SEQUENCE: 6

Ala Arg Glu Gly Tyr Gly Tyr Gly Lys Asn Gly Val Gly Tyr Ala Met
1               5                   10                  15

Asp Tyr

<210> SEQ ID NO 7
<211> LENGTH: 6
<212> TYPE: PRT
<213> ORGANISM: Artificial Sequence
<220> FEATURE:
<223> OTHER INFORMATION: synthesized

<400> SEQUENCE: 7

Gln Asp Ile Asn Lys Tyr
1               5

<210> SEQ ID NO 8
<211> LENGTH: 3
<212> TYPE: PRT
<213> ORGANISM: Artificial Sequence
<220> FEATURE:
<223> OTHER INFORMATION: synthesized

<400> SEQUENCE: 8

Ser Thr Ser
1

<210> SEQ ID NO 9
<211> LENGTH: 8
<212> TYPE: PRT
<213> ORGANISM: Artificial Sequence
<220> FEATURE:
<223> OTHER INFORMATION: synthesized

<400> SEQUENCE: 9

Leu Gln Tyr Asp Asp Leu Phe Thr
1               5

<210> SEQ ID NO 10
<211> LENGTH: 6
<212> TYPE: PRT
<213> ORGANISM: Artificial Sequence
<220> FEATURE:
<223> OTHER INFORMATION: synthesized

<400> SEQUENCE: 10

Gln Ser Val Ser Asn Asp
1               5

<210> SEQ ID NO 11
<211> LENGTH: 3
<212> TYPE: PRT
<213> ORGANISM: Artificial Sequence
<220> FEATURE:
<223> OTHER INFORMATION: synthesized

<400> SEQUENCE: 11
```

-continued

```
Tyr Ala Ser
1

<210> SEQ ID NO 12
<211> LENGTH: 9
<212> TYPE: PRT
<213> ORGANISM: Artificial Sequence
<220> FEATURE:
<223> OTHER INFORMATION: synthesized

<400> SEQUENCE: 12

Gln Gln Asp Tyr Ser Ser Pro Trp Thr
1               5

<210> SEQ ID NO 13
<211> LENGTH: 467
<212> TYPE: PRT
<213> ORGANISM: Artificial Sequence
<220> FEATURE:
<223> OTHER INFORMATION: synthesized

<400> SEQUENCE: 13

Met Gly Trp Ser Trp Val Phe Leu Phe Leu Leu Ser Val Thr Ala Gly
1               5                   10                  15

Val His Ser Gln Val Gln Leu Gln Gln Ser Gly Ala Glu Leu Val Lys
                20                  25                  30

Pro Gly Ala Ser Val Lys Leu Ser Cys Lys Ala Ser Gly Tyr Thr Phe
            35                  40                  45

Thr Ser Phe Asp Ile Asn Trp Val Arg Gln Arg Pro Glu Gln Gly Leu
        50                  55                  60

Glu Trp Ile Gly Trp Ile Phe Pro Gly Asp Gly Asn Thr Lys Ser Asn
65                  70                  75                  80

Glu Lys Phe Lys Gly Lys Ala Thr Leu Thr Thr Asp Lys Ser Ser Ser
                85                  90                  95

Thr Ala Tyr Met Gln Leu Ser Arg Leu Thr Ser Glu Asp Ser Ala Val
                100                 105                 110

Tyr Phe Cys Val Arg Gly Glu Ala Leu Tyr Tyr Phe Asp Tyr Trp Gly
            115                 120                 125

Pro Gly Thr Thr Leu Thr Val Ser Ser Ala Ser Thr Lys Gly Pro Ser
        130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
        210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285
```

```
Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
    450                 455                 460

Pro Gly Lys
465

<210> SEQ ID NO 14
<211> LENGTH: 233
<212> TYPE: PRT
<213> ORGANISM: Artificial Sequence
<220> FEATURE:
<223> OTHER INFORMATION: synthesized

<400> SEQUENCE: 14

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
                20                  25                  30

Ala Ser Leu Gly Gly Lys Val Thr Ile Thr Cys Lys Pro Ser Gln Asp
            35                  40                  45

Ile Asn Lys Tyr Ile Ala Trp Tyr Gln His Lys Pro Gly Lys Gly Pro
    50                  55                  60

Arg Leu Leu Ile His Ser Thr Ser Thr Leu Gln Pro Gly Ile Pro Ser
65                  70                  75                  80

Arg Phe Ser Gly Ser Gly Ser Gly Arg Asp Tyr Ser Phe Thr Ile Ser
                85                  90                  95

Asn Leu Glu Pro Glu Asp Ile Ala Thr Tyr Tyr Cys Leu Gln Tyr Asp
                100                 105                 110

Asp Leu Phe Thr Phe Gly Ser Gly Thr Lys Leu Glu Ile Lys Arg Thr
            115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175
```

-continued

```
Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
            210                 215                 220

Thr Lys Ser Phe Asn Arg Gly Glu Cys
225                 230

<210> SEQ ID NO 15
<211> LENGTH: 473
<212> TYPE: PRT
<213> ORGANISM: Artificial Sequence
<220> FEATURE:
<223> OTHER INFORMATION: synthesized

<400> SEQUENCE: 15

Met Glu Trp Arg Ile Phe Leu Phe Ile Leu Ser Gly Thr Ala Gly Val
1               5                   10                  15

His Ser Gln Val Gln Leu Gln Gln Ser Gly Pro Glu Val Val Lys Pro
            20                  25                  30

Gly Ala Ser Val Lys Met Ser Cys Lys Ala Ser Gly Tyr Thr Phe Thr
            35                  40                  45

Asp His Val Ile Ser Trp Val Lys Gln Arg Thr Gly Gln Gly Leu Glu
            50                  55                  60

Trp Ile Gly Gln Ile Tyr Pro Gly Ser Asp Asn Ser Tyr Tyr Ser Glu
65                  70                  75                  80

Lys Leu Lys Asp Lys Ala Thr Leu Thr Ala Asp Lys Ser Ser Asn Thr
            85                  90                  95

Ala Tyr Met Gln Leu Val Ser Leu Thr Ser Glu Asp Ser Ala Val Tyr
            100                 105                 110

Phe Cys Ala Arg Glu Gly Tyr Gly Tyr Gly Lys Asn Gly Val Gly Tyr
            115                 120                 125

Ala Met Asp Tyr Trp Gly Gln Gly Thr Ser Val Thr Val Ser Ser Ala
            130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
            165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
            210                 215                 220

Ile Cys Asn Val Asn His Lys Pro Ser Asn Thr Lys Val Asp Lys Arg
225                 230                 235                 240

Val Glu Pro Lys Ser Cys Asp Lys Thr His Thr Cys Pro Pro Cys Pro
            245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
            290                 295                 300
```

```
Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Glu Glu Met
        370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
        450                 455                 460

Lys Ser Leu Ser Leu Ser Pro Gly Lys
465                 470
```

```
<210> SEQ ID NO 16
<211> LENGTH: 234
<212> TYPE: PRT
<213> ORGANISM: Artificial Sequence
<220> FEATURE:
<223> OTHER INFORMATION: synthesized

<400> SEQUENCE: 16

Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
            20                  25                  30

Val Ser Ala Gly Asp Arg Val Thr Ile Thr Cys Lys Ala Ser Gln Ser
        35                  40                  45

Val Ser Asn Asp Val Val Trp Tyr Gln Gln Lys Pro Gly Gln Ser Pro
    50                  55                  60

Lys Leu Leu Ile Tyr Tyr Ala Ser Asn Arg Tyr Thr Gly Val Pro Asp
65                  70                  75                  80

Arg Phe Thr Gly Ser Gly Tyr Gly Thr Asp Phe Thr Phe Thr Ile Ser
                85                  90                  95

Thr Ala Gln Ala Glu Asp Leu Ala Val Tyr Phe Cys Gln Gln Asp Tyr
            100                 105                 110

Ser Ser Pro Trp Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190
```

```
Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 17
<211> LENGTH: 466
<212> TYPE: PRT
<213> ORGANISM: Artificial Sequence
<220> FEATURE:
<223> OTHER INFORMATION: synthesized

<400> SEQUENCE: 17

Met Gly Trp Ser Trp Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Leu Ser Cys Lys Ala Ser Gly Tyr Thr Phe
        35                  40                  45

Thr Ser Phe Asp Ile Asn Trp Val Arg Gln Ala Pro Glu Gln Arg Leu
    50                  55                  60

Glu Trp Met Gly Trp Ile Phe Pro Gly Asp Gly Asn Thr Lys Tyr Ser
65                  70                  75                  80

Gln Lys Phe Gln Gly Arg Ala Thr Ile Thr Arg Asp Thr Ser Ala Ser
            85                  90                  95

Thr Ala Tyr Met Glu Leu Ser Ser Leu Arg Ser Glu Asp Thr Ala Val
            100                 105                 110

Tyr Tyr Cys Val Arg Gly Glu Ala Leu Tyr Tyr Phe Asp Tyr Trp Gly
            115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
            290                 295                 300

His Asn Ala Lys Thr Lys Pro Arg Glu Glu Gln Tyr Asn Ser Thr Tyr
305                 310                 315                 320
```

-continued

```
Arg Val Val Ser Val Leu Thr Val Leu His Gln Asp Trp Leu Asn Gly
                325             330             335

Lys Glu Tyr Lys Cys Lys Val Ser Asn Lys Ala Leu Pro Ala Pro Ile
            340             345             350

Glu Lys Thr Ile Ser Lys Ala Lys Gly Gln Pro Arg Glu Pro Gln Val
        355             360             365

Tyr Thr Leu Pro Pro Ser Arg Asp Glu Leu Thr Lys Asn Gln Val Ser
    370             375             380

Leu Thr Cys Leu Val Lys Gly Phe Tyr Pro Ser Asp Ile Ala Val Glu
385             390             395             400

Trp Glu Ser Asn Gly Gln Pro Glu Asn Asn Tyr Lys Thr Thr Pro Pro
                405             410             415

Val Leu Asp Ser Asp Gly Ser Phe Phe Leu Tyr Ser Lys Leu Thr Val
            420             425             430

Asp Lys Ser Arg Trp Gln Gln Gly Asn Val Phe Ser Cys Ser Val Met
        435             440             445

His Glu Ala Leu His Asn His Tyr Thr Gln Lys Ser Leu Ser Leu Ser
    450             455             460

Pro Gly
465
```

```
<210> SEQ ID NO 18
<211> LENGTH: 233
<212> TYPE: PRT
<213> ORGANISM: Artificial Sequence
<220> FEATURE:
<223> OTHER INFORMATION: synthesized

<400> SEQUENCE: 18

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Asn Lys Tyr Leu Ala Trp Tyr Gln Gln Lys Pro Gly Lys Val Pro
    50                  55                  60

Lys Leu Leu Ile Tyr Ser Thr Ser Thr Leu Gln Ser Gly Val Pro Ser
65                  70                  75                  80

Arg Phe Ser Gly Ser Gly Ser Gly Thr Asp Phe Thr Leu Thr Ile Ser
            85                  90                  95

Ser Leu Gln Pro Glu Asp Val Ala Thr Tyr Tyr Cys Leu Gln Tyr Asp
            100                 105                 110

Asp Leu Phe Thr Phe Gly Gln Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
            165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205
```

-continued

```
Lys Val Tyr Ala Cys Glu Val Thr His Gln Gly Leu Ser Ser Pro Val
    210             215             220

Thr Lys Ser Phe Asn Arg Gly Glu Cys
225             230

<210> SEQ ID NO 19
<211> LENGTH: 472
<212> TYPE: PRT
<213> ORGANISM: Artificial Sequence
<220> FEATURE:
<223> OTHER INFORMATION: synthesized

<400> SEQUENCE: 19

Met Glu Trp Arg Ile Phe Leu Phe Ile Leu Ser Gly Thr Ala Gly Val
1               5               10              15

His Ser Gln Val Gln Leu Val Gln Ser Gly Ala Glu Val Lys Lys Pro
                20              25              30

Gly Ala Ser Val Lys Val Ser Cys Lys Ala Ser Gly Tyr Thr Phe Thr
            35              40              45

Asp His Val Ile Ser Trp Val Arg Gln Ala Thr Gly Gln Gly Leu Glu
    50              55              60

Trp Met Gly Gln Ile Tyr Pro Gly Ser Asp Asn Ser Tyr Tyr Ala Gln
65              70              75              80

Lys Phe Gln Gly Arg Val Thr Leu Thr Ala Asp Lys Ser Ile Asn Thr
                85              90              95

Ala Tyr Met Glu Leu Ser Ser Leu Arg Ser Glu Asp Thr Ala Val Tyr
            100             105             110

Tyr Cys Ala Arg Glu Gly Tyr Gly Tyr Gly Lys Asn Gly Val Gly Tyr
        115             120             125

Ala Met Asp Tyr Trp Gly Gln Gly Thr Leu Val Thr Val Ser Ser Ala
    130             135             140

Ser Thr Lys Gly Pro Ser Val Phe Pro Leu Ala Pro Ser Ser Lys Ser
145             150             155             160

Thr Ser Gly Gly Thr Ala Ala Leu Gly Cys Leu Val Lys Asp Tyr Phe
                165             170             175

Pro Glu Pro Val Thr Val Ser Trp Asn Ser Gly Ala Leu Thr Ser Gly
            180             185             190

Val His Thr Phe Pro Ala Val Leu Gln Ser Ser Gly Leu Tyr Ser Leu
        195             200             205

Ser Ser Val Val Thr Val Pro Ser Ser Ser Leu Gly Thr Gln Thr Tyr
    210             215             220

Ile Cys Asn Val Asn His Lys Pro Ser Asn Thr Lys Val Asp Lys Arg
225             230             235             240

Val Glu Pro Lys Ser Cys Asp Lys Thr His Thr Cys Pro Pro Cys Pro
                245             250             255

Ala Pro Glu Leu Leu Gly Gly Pro Ser Val Phe Leu Phe Pro Pro Lys
            260             265             270

Pro Lys Asp Thr Leu Met Ile Ser Arg Thr Pro Glu Val Thr Cys Val
        275             280             285

Val Val Asp Val Ser His Glu Asp Pro Glu Val Lys Phe Asn Trp Tyr
    290             295             300

Val Asp Gly Val Glu Val His Asn Ala Lys Thr Lys Pro Arg Glu Glu
305             310             315             320

Gln Tyr Asn Ser Thr Tyr Arg Val Val Ser Val Leu Thr Val Leu His
                325             330             335
```

```
Gln Asp Trp Leu Asn Gly Lys Glu Tyr Lys Cys Lys Val Ser Asn Lys
        340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
        370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
                420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
        450                 455                 460

Lys Ser Leu Ser Leu Ser Pro Gly
465                 470

<210> SEQ ID NO 20
<211> LENGTH: 234
<212> TYPE: PRT
<213> ORGANISM: Artificial Sequence
<220> FEATURE:
<223> OTHER INFORMATION: synthesized

<400> SEQUENCE: 20

Met Lys Ser Gln Thr Gln Val Phe Val Phe Leu Leu Leu Cys Val Ser
1                 5                   10                  15

Gly Ala His Gly Asp Ile Val Met Thr Gln Ser Pro Asp Ser Leu Ala
                20                  25                  30

Val Ser Leu Gly Glu Arg Ala Thr Ile Asn Cys Lys Ala Ser Gln Ser
        35                  40                  45

Val Ser Asn Asp Val Val Trp Tyr Gln Gln Lys Pro Gly Gln Pro Pro
        50                  55                  60

Lys Leu Leu Ile Tyr Tyr Ala Ser Asn Arg Tyr Thr Gly Val Pro Asp
65                  70                  75                  80

Arg Phe Ser Gly Ser Gly Tyr Gly Thr Asp Phe Thr Leu Thr Ile Ser
                85                  90                  95

Ser Leu Gln Ala Glu Asp Val Ala Val Tyr Tyr Cys Gln Gln Asp Tyr
                100                 105                 110

Ser Ser Pro Trp Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
        210                 215                 220
```

```
Val Thr Lys Ser Phe Asn Arg Gly Glu Cys
225                 230

<210> SEQ ID NO 21
<211> LENGTH: 24
<212> TYPE: DNA
<213> ORGANISM: Artificial Sequence
<220> FEATURE:
<223> OTHER INFORMATION: synthesized

<400> SEQUENCE: 21
ggctacacct tcacaagctt tgat                                        24

<210> SEQ ID NO 22
<211> LENGTH: 21
<212> TYPE: DNA
<213> ORGANISM: Artificial Sequence
<220> FEATURE:
<223> OTHER INFORMATION: synthesized

<400> SEQUENCE: 22
atttttcctg gagatggtaa t                                          21

<210> SEQ ID NO 23
<211> LENGTH: 33
<212> TYPE: DNA
<213> ORGANISM: Artificial Sequence
<220> FEATURE:
<223> OTHER INFORMATION: synthesized

<400> SEQUENCE: 23
gtaagagggg aggccctgta ttactttgac tac                             33

<210> SEQ ID NO 24
<211> LENGTH: 24
<212> TYPE: DNA
<213> ORGANISM: Artificial Sequence
<220> FEATURE:
<223> OTHER INFORMATION: synthesized

<400> SEQUENCE: 24
ggatacacat tcactgacca tgtc                                       24

<210> SEQ ID NO 25
<211> LENGTH: 24
<212> TYPE: DNA
<213> ORGANISM: Artificial Sequence
<220> FEATURE:
<223> OTHER INFORMATION: synthesized

<400> SEQUENCE: 25
atttatcctg gaagtgataa tagt                                       24

<210> SEQ ID NO 26
<211> LENGTH: 54
<212> TYPE: DNA
<213> ORGANISM: Artificial Sequence
<220> FEATURE:
<223> OTHER INFORMATION: synthesized

<400> SEQUENCE: 26
gcaagagagg gctatggtta tggaaaaaac ggagttggct atgctatgga ctac        54

<210> SEQ ID NO 27
<211> LENGTH: 18
```

```
<212> TYPE: DNA
<213> ORGANISM: Artificial Sequence
<220> FEATURE:
<223> OTHER INFORMATION: synthesized

<400> SEQUENCE: 27
caagacatta ataagtat                                                    18

<210> SEQ ID NO 28
<211> LENGTH: 9
<212> TYPE: DNA
<213> ORGANISM: Artificial Sequence
<220> FEATURE:
<223> OTHER INFORMATION: synthesized

<400> SEQUENCE: 28 tccacatct                                                              9

<210> SEQ ID NO 29
<211> LENGTH: 24
<212> TYPE: DNA
<213> ORGANISM: Artificial Sequence
<220> FEATURE:
<223> OTHER INFORMATION: synthesized

<400> SEQUENCE: 29
ctgcagtatg atgatctatt cacg                                             24

<210> SEQ ID NO 30
<211> LENGTH: 18
<212> TYPE: DNA
<213> ORGANISM: Artificial Sequence
<220> FEATURE:
<223> OTHER INFORMATION: synthesized

<400> SEQUENCE: 30
cagagtgtga gtaatgat                                                    18

<210> SEQ ID NO 31
<211> LENGTH: 9
<212> TYPE: DNA
<213> ORGANISM: Artificial Sequence
<220> FEATURE:
<223> OTHER INFORMATION: synthesized

<400> SEQUENCE: 31 tatgcatcc                                                              9

<210> SEQ ID NO 32
<211> LENGTH: 27
<212> TYPE: DNA
<213> ORGANISM: Artificial Sequence
<220> FEATURE:
<223> OTHER INFORMATION: synthesized

<400> SEQUENCE: 32
cagcaggatt attcctctcc gtggacg                                          27

<210> SEQ ID NO 33
<211> LENGTH: 1404
<212> TYPE: DNA
<213> ORGANISM: Artificial Sequence
<220> FEATURE:
<223> OTHER INFORMATION: synthesized

<400> SEQUENCE: 33
```

-continued

```
atgggatgga gctgggtctt tctcttcctc ctgtcagtaa ctgcaggtgt ccactcccag    60
gttcagctgc agcagtctgg agctgaactg gtaaagcctg gggcttcagt gaagttgtcc    120
tgcaaggctt ctggctacac cttcacaagc tttgatataa actgggtgag gcagaggcct    180
gaacagggac ttgagtggat tggatggatt tttcctggag atggtaatac taagtccaat    240
gagaaattta agggcaaggc cacactgact acagacaaat cctccagcac agcctacatg    300
cagctcagca ggctgacatc tgaggactct gctgtctatt tctgtgtaag aggggaggcc    360
ctgtattact ttgactactg gggcccaggc accactctca cagtctcctc agctagcacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga gagttgagcc caaatcttgt    720
gacaaaactc acacatgccc accgtgccca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag    1020
tgcaaggtct ccaacaaagc cctcccagcc cccatcgaga aaaccatctc caaagccaaa    1080
gggcagcccc gagaaccaca ggtgtacacc ctgcccccat cccgggagga tgaccaag    1140 aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta tagcaagctc accgtggaca gagcaggtg gcagcagggg    1320 aacgtcttct catgctccgt gatgcatgag gctctgcaca accactacac gcagaagagc    1380
ctctccctgt ctccgggtaa atga    1404
```

<210> SEQ ID NO 34
<211> LENGTH: 702
<212> TYPE: DNA
<213> ORGANISM: Artificial Sequence
<220> FEATURE:
<223> OTHER INFORMATION: synthesized

<400> SEQUENCE: 34

```
atgagaccgt ctattcagtt cctggggctc ttgttgttct ggcttcatgg tgctcagtgt    60
gacatccaga tgacacagtc tccatcctca ctgtctgcat ctctgggagg caaagtcacc    120
atcacttgca agccaagcca agacattaat aagtatatag cttggtacca acacaagcct    180
ggaaaaggtc ctaggctgct catacattcc acatctacat tacagccagg catcccatca    240
aggttcagtg gaagtgggtc tgggagagat tattccttca ccatcagcaa cctggaacct    300
gaagatattg caacttatta ttgtctgcag tatgatgatc tattcacgtt cggctcgggg    360
acaaagttgg aaataaaacg tacggtggct gcaccatctg tcttcatctt cccgccatct    420
gatgagcagt tgaaatctgg aactgcctct gttgtgtgcc tgctgaataa cttctatccc    480
agagaggcca agtacagtg gaaggtggat aacgccctcc aatcgggtaa ctcccaggag    540
agtgtcacag agcaggacag caaggacagc acctacagcc tcagcagcac cctgacgctg    600
agcaaagcag actacgagaa acacaaagtc tacgcctgcg aagtcaccca tcagggcctg    660
```

-continued

```
agctcgcccg tcacaaagag cttcaacagg ggagagtgtt ag                  702

<210> SEQ ID NO 35
<211> LENGTH: 1422
<212> TYPE: DNA
<213> ORGANISM: Artificial Sequence
<220> FEATURE:
<223> OTHER INFORMATION: synthesized

<400> SEQUENCE: 35
atggaatgga ggatctttct cttcatcctg tcaggaactg caggtgtcca ctcccaggtt   60
cagctgcagc agtctggacc tgaggtggtg aagcctgggg cttcagtgaa gatgtcctgc  120
aaggcttctg gatacacatt cactgaccat gtcataagct gggtgaagca gagaactgga  180
cagggccttg agtggattgg acagatttat cctggaagtg ataatagtta ctacagtgag  240
aagttgaagg acaaggccac actgactgca gacaaatcct ccaacacagc ctacatgcag  300
ctcgtcagcc tgacatctga ggactctgcg gtctatttct gtgcaagaga gggctatggt  360
tatggaaaaa acggagttgg ctatgctatg gactactggg gtcaaggaac ctcagtcacc  420
gtctcctcag ctagcaccaa gggcccatcg gtcttccccc tggcaccctc ctccaagagc  480
acctctgggg gcacagcggc cctgggctgc ctggtcaagg actacttccc cgaaccggtg  540
acggtgtcgt ggaactcagg cgccctgacc agcggcgtgc acaccttccc ggctgtccta  600
cagtcctcag gactctactc cctcagcagc gtggtgaccg tgccctccag cagcttgggc  660
acccagacct acatctgcaa cgtgaatcac aagcccagca acaccaaggt ggacaagaga  720
gttgagccca atcttgtga  caaaaactcac acatgcccac cgtgcccagc acctgaactc  780
ctggggggac cgtcagtctt cctcttcccc ccaaaaccca aggacaccct catgatctcc  840
cggacccctg aggtcacatg cgtggtggtg gacgtgagcc acgaagaccc tgaggtcaag  900
ttcaactggt acgtggacgg cgtggaggtg cataatgcca agacaaagcc gcgggaggag  960
cagtacaaca gcacgtaccg tgtggtcagc gtcctcaccg tcctgcacca ggactggctg 1020
aatggcaagg agtacaagtg caaggtctcc aacaaagccc tcccagcccc catcgagaaa 1080
accatctcca aagccaaagg gcagccccga gaaccacagg tgtacaccct gcccccatcc 1140
cgggaggaga tgaccaagaa ccaggtcagc ctgacctgcc tggtcaaagg cttctatccc 1200
agcgacatcg ccgtggagtg ggagagcaat gggcagccgg agaacaacta caagaccacg 1260
cctcccgtgc tggactccga cggctccttc ttcctctata gcaagctcac cgtggacaag 1320
agcaggtggc agcaggggaa cgtcttctca tgctccgtga tgcatgaggc tctgcacaac 1380
cactacacgc agaagagcct ctccctgtct ccgggtaaat ga                   1422

<210> SEQ ID NO 36
<211> LENGTH: 705
<212> TYPE: DNA
<213> ORGANISM: Artificial Sequence
<220> FEATURE:
<223> OTHER INFORMATION: synthesized

<400> SEQUENCE: 36
atgaagtcac agacccaggt cttcgtattt ctactgctct gtgtgtctgg tgctcatggg   60
agtattgtga tgacccagac tcccaaattc ctgcttgtat cagcaggaga cagggttacc  120
ataacctgca aggccagtca gagtgtgagt aatgatgtag tttggtacca acagaagcca  180
gggcagtctc ctaaactgct gatatactat gcatccaatc gctacactgg agtccctgat  240
```

-continued

```
cgcttcaccg gcagtggata tgggacggat ttcactttca ccatcagcac tgcgcaggct        300
gaagacctgg cagtttattt ctgtcagcag gattattcct ctccgtggac gttcggtggg        360
ggcaccaagc tggaaatcaa acgtacggtg gctgcaccat ctgtcttcat cttcccgcca        420
tctgatgagc agttgaaatc tggaactgcc tctgttgtgt gcctgctgaa taacttctat        480
cccagagagg ccaaagtaca gtggaaggtg gataacgccc tccaatcggg taactcccag        540
gagagtgtca cagagcagga cagcaaggac agcacctaca gcctcagcag caccctgacg        600
ctgagcaaag cagactacga gaaacacaaa gtctacgcct gcgaagtcac ccatcagggc        660
ctgagctcgc ccgtcacaaa gagcttcaac aggggagagt gttag                        705
```

```
<210> SEQ ID NO 37
<211> LENGTH: 1401
<212> TYPE: DNA
<213> ORGANISM: Artificial Sequence
<220> FEATURE:
<223> OTHER INFORMATION: synthesized

<400> SEQUENCE: 37
```

```
atgggctggt cctgggtgtt cctgttcctg ctgagcgtga ccgccggcgt gcactcccag         60
gtgcagctgg tgcagtccgg cgccgaggtg aagaagcccg gcgcctccgt gaagctgagc        120
tgtaaggcct ccggctacac cttcacctcc ttcgacatta actgggtgcg gcaggccccc        180
gagcagcgcc tggagtggat gggctggatc ttccccggcg acggcaacac caagtactcc        240
cagaagttcc agggaagagc taccatcacc agagatacat ccgcttctac agcttacatg        300
gagctgtcta gcctgagatc tgaggataca gctgtgtatt actgtgtgag aggagaggct        360
ctgtactatt ttgattattg gggccagggc accctggtga cagtgtcttc tgctagcacc        420
aagggcccat cggtcttccc cctggcaccc tcctccaaga gcacctctgg gggcacagcg        480
gccctgggct gcctggtcaa ggactacttc cccgaaccgg tgacggtgtc gtggaactca        540
ggcgccctga ccagcggcgt gcacaccttc ccggctgtcc tacagtcctc aggactctac        600
tccctcagca gcgtggtgac cgtgccctcc agcagcttgg gcacccagac ctacatctgc        660
aacgtgaatc acaagcccag caacaccaag gtggacaaga gagttgagcc caaatcttgt        720
gacaaaactc acacatgccc accgtgccca gcacctgaac tcctgggggg accgtcagtc        780
ttcctcttcc ccccaaaacc caaggacacc ctcatgatct cccggacccc tgaggtcaca        840
tgcgtggtgg tggacgtgag ccacgaagac cctgaggtca agttcaactg gtacgtggac        900
ggcgtggagg tgcataatgc caagacaaag ccgcgggagg agcagtacaa cagcacgtac        960
cgtgtggtca gcgtcctcac cgtcctgcac caggactggc tgaatggcaa ggagtacaag       1020
tgcaaggtct ccaacaaagc cctcccagcc cccatcgaga aaaccatctc caaagccaaa       1080
gggcagcccc gagaaccaca ggtgtacacc ctgcccccat cccgggatga gctgaccaag       1140
aaccaggtca gcctgacctg cctggtcaaa ggcttctatc ccagcgacat cgccgtggag       1200
tgggagagca atgggcagcc ggagaacaac tacaagacca cgcctcccgt gctggactcc       1260
gacggctcct tcttcctcta tagcaagctc accgtggaca gagcaggtg gcagcagggg        1320 aacgtcttct catgctccgt gatgcatgag gctctgcaca accactacac gcagaagagc       1380
ctctccctgt ctccgggtta a                                                 1401
```

```
<210> SEQ ID NO 38
<211> LENGTH: 702
<212> TYPE: DNA
<213> ORGANISM: Artificial Sequence
```

```
<220> FEATURE:
<223> OTHER INFORMATION: synthesized

<400> SEQUENCE: 38
atgagacctt ctatccagtt tctgggcctg ctgctgtttt ggctgcatgg cgcccagtgc      60
gatatccaga tgacccagtc tccatctagc ctgtccgctt ctgtgggcga tagagtgacc     120
atcacatgca gagcttctca ggatatcaat aagtatctgg cttggtatca gcagaagcct     180
ggaaaggtgc ctaagctgct gatctactct acatctaccc tgcagtctgg agtgccttct     240
agattttctg gatctggctc tggcaccgat tttacactga caatctcttc tctgcagcct     300
gaggatgtgg ctacatatta ttgtctgcag tatgatgatc tgttcacctt tggccagggc     360
accaagctgg agatcaagcg tacggtggct gcaccatctg tcttcatctt cccgccatct     420
gatgagcagt tgaaatctgg aactgcctct gttgtgtgcc tgctgaataa cttctatccc     480
agagaggcca agtacagtg gaaggtggat aacgccctcc aatcgggtaa ctcccaggag     540
agtgtcacag agcaggacag caaggacagc acctacagcc tcagcagcac cctgacgctg     600
agcaaagcag actacgagaa acacaaagtc tacgcctgcg aagtcaccca tcagggcctg     660
agctcgcccg tcacaaagag cttcaacagg ggagagtgtt ag                        702

<210> SEQ ID NO 39
<211> LENGTH: 1419
<212> TYPE: DNA
<213> ORGANISM: Artificial Sequence
<220> FEATURE:
<223> OTHER INFORMATION: synthesized

<400> SEQUENCE: 39
atggagtgga gaatctttct gtttatcctg tctggcacag ctggagtgca ttctcaggtg      60
cagctggtgc agtctggggc cgaggtgaaa aagccaggcg cttctgtgaa ggtgtcttgc     120
aaggcctccg gctacacctt caccgaccac gtgatctcct gggtgcgcca ggccaccggc     180
cagggcctgg agtggatggg ccagatctac cccggctccg acaactccta ctacgcccag     240
aagttccagg gcagggtgac tctgaccgcc gacaagtcca tcaacaccgc ctacatggag     300
ctgtcctccc tgaggtccga ggacaccgcc gtgtactact cgccaggga gggctacggc     360 tacggcaaga acggcgtggg ctacgccatg gattattggg gccagggcac cctggtgaca     420
gtgtcttctg ctagcaccaa gggcccatcg gtcttccccc tggcaccctc tccaagagc     480 acctctgggg gcacagcggc cctgggctgc ctggtcaagg actacttccc cgaaccggtg     540
acggtgtcgt ggaactcagg cgccctgacc agcggcgtgc acaccttccc ggctgtccta     600
cagtcctcag gactctactc cctcagcagc gtggtgaccg tgccctccag cagcttgggc     660
acccagacct acatctgcaa cgtgaatcac aagcccagca acaccaaggt ggacaagaga     720
gttgagccca atcttgtga caaaactcac acatgcccac cgtgcccagc acctgaactc     780
ctggggggac cgtcagtctt cctcttcccc ccaaaaccca aggacaccct catgatctcc     840
cggacccctg aggtcacatg cgtggtggtg gacgtgagcc acgaagaccc tgaggtcaag     900
ttcaactggt acgtggacgg cgtggaggtg cataatgcca agacaaagcc gcgggaggag     960
cagtacaaca gcacgtaccg tgtggtcagc gtcctcaccg tcctgcacca ggactggctg    1020
aatggcaagg agtacaagtg caaggtctcc aacaaagccc tcccagcccc catcgagaaa    1080
accatctcca aagccaaagg gcagccccga gaaccacagg tgtacaccct gcccccatcc    1140
cgggatgagc tgaccaagaa ccaggtcagc ctgacctgcc tggtcaaagg cttctatccc    1200
```

-continued

```
agcgacatcg ccgtggagtg ggagagcaat gggcagccgg agaacaacta caagaccacg      1260
cctcccgtgc tggactccga cggctccttc ttcctctata gcaagctcac cgtggacaag      1320
agcaggtggc agcaggggaa cgtcttctca tgctccgtga tgcatgaggc tctgcacaac      1380
cactacacgc agaagagcct ctccctgtct ccgggttaa                            1419
```

<210> SEQ ID NO 40
<211> LENGTH: 705
<212> TYPE: DNA
<213> ORGANISM: Artificial Sequence
<220> FEATURE:
<223> OTHER INFORMATION: synthesized

<400> SEQUENCE: 40

```
atgaagtctc agacccaggt gtttgtgttt ctgctgctgt gtgtgtctgg cgctcatggc        60
gatatcgtga tgacacagtc tcctgattct ctggccgtgt ctctgggcga aagagctaca       120
atcaactgta aggcttctca gtctgtgtct aatgatgtgg tgtggtacca gcagaagcct       180
gggcagcccc ccaagctgct gatctactac gcctccaaca ggtacaccgg cgtgcccgac       240
aggttctccg gctccggcta cggcaccgac ttcaccctga ccatctcctc cctgcaggcc       300
gaggacgtgg ccgtgtacta ctgccagcag gactactcct cccctggac cttcggcggc        360 ggcaccaagg tggagatcaa gcgtacggtg gctgcaccat ctgtcttcat cttcccgcca       420
tctgatgagc agttgaaatc tggaactgcc tctgttgtgt gcctgctgaa taacttctat       480
cccagagagg ccaaagtaca gtggaaggtg gataacgccc tccaatcggg taactcccag       540
gagagtgtca cagagcagga cagcaaggac agcacctaca gcctcagcag caccctgacg       600
ctgagcaaag cagactacga gaaacacaaa gtctacgcct gcgaagtcac ccatcagggc       660
ctgagctcgc ccgtcacaaa gagcttcaac aggggagagt gttag                      705
```